US010125162B2

(12) United States Patent
Krauss et al.

(10) Patent No.: US 10,125,162 B2
(45) Date of Patent: *Nov. 13, 2018

(54) METHODS FOR THE DEVELOPMENT OF VACCINES BASED ON OLIGOSACCHARIDE-OLIGONUCLEOTIDE CONJUGATES

(71) Applicant: Brandeis University, Waltham, MA (US)

(72) Inventors: Isaac J. Krauss, Waltham, MA (US); Lizbeth K. Hedstrom, Newton, MA (US); Iain S. MacPherson, Honolulu, HI (US)

(73) Assignee: Brandeis University, Waltham, MA (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/744,985

(22) Filed: Jun. 19, 2015

(65) Prior Publication Data

US 2016/0051690 A1 Feb. 25, 2016

Related U.S. Application Data

(63) Continuation of application No. 13/701,849, filed as application No. PCT/US2011/039949 on Jun. 10, 2011, now Pat. No. 9,080,169.

(60) Provisional application No. 61/353,857, filed on Jun. 11, 2010.

(51) Int. Cl.
*C07H 21/04* (2006.01)
*C12N 15/10* (2006.01)
*C07H 15/22* (2006.01)
*A61K 39/21* (2006.01)
*A61K 47/48* (2006.01)
*C12N 7/00* (2006.01)
*A61K 39/00* (2006.01)

(52) U.S. Cl.
CPC ............ *C07H 21/04* (2013.01); *A61K 39/21* (2013.01); *A61K 47/4833* (2013.01); *C07H 15/22* (2013.01); *C12N 7/00* (2013.01); *C12N 15/1048* (2013.01); *C12N 15/1058* (2013.01); *A61K 2039/55505* (2013.01); *A61K 2039/55511* (2013.01); *A61K 2039/6068* (2013.01); *A61K 2039/6081* (2013.01); *A61K 2039/627* (2013.01)

(58) Field of Classification Search
CPC .................................................... C07H 21/04
USPC .................................. 536/23.1; 514/44 A
See application file for complete search history.

(56) References Cited

U.S. PATENT DOCUMENTS 9,080,169 B2 * 7/2015 Krauss
2009/0136522 A1 5/2009 Haynes et al.
2009/0311289 A1 12/2009 Haynes et al.

FOREIGN PATENT DOCUMENTS

EP 1489171 A1 12/2004
WO WO 2006/104530 * 10/2006

OTHER PUBLICATIONS

Astronomo et al., "Defining Criteria for Oligomannose Immunogens for HIV Using Icosahedral Virus Capsid Scaffolds," Chemistry & Biology 17:357-370 (2010).
Cannata et al., "Triplex-forming Oligonucleotide-orthphenanthroline Conjugates for Efficient Targeted Genome Modification," PNAS 105(28):9576-9581 (2008).
Crich et al., "Direct Synthesis of β-Mannans. A Hexameric [arrow3)-β-D-Man-(1arrow4)-β-D-Man-(1]3 Subunit of the Antigenic Polysacharides from Leptospira biflexa and the Octameric (1arrow2)-Linked β-D-Mannan of the Candida albicans Phospholipomannan. X-ray Crystal Structure of a Protected Tetramer," Journal of the American Chemical Society 123(24):5826-5828 (2001).
Gallo et al., "Design and Applications of Modified Olignucleotides," Brazillian Journal of Medical and Biological Research 36:143-151 (2003).
Geng et al., "In Pursuit of Carbohydrate-based HIV Vaccines, Part 2: The Total Synthesis of High-Mannose-Type gp120 Fragments—Evaluation of Strategies Directed to Maximal Convergence," Agnew. Chem. Int. Ed. 43 (19):2562-2565 (2004).
Guo et al., "CELL-SELEX: Novel Perspectives of Aptamer-Based Therapeutics," Int. J. Mol. Sci. 9:668-678 (2008).
Ichida et al., "An In vitro Selection System for TNA," J. Am. Chem. Soc. 127:2802-2803 (2005).
Keefe et al., "SELEX with Mofidied Nucleotides," Current Opinion in Chemical Biology 12:448-456 (2008).
Kolb et al., "Click Chemistry: Diverse Chemical Function from a Few Good Reactions," Angew. Chem. Int. Ed. 40 (11):2004-2021 (2001).
Kuijpers et al., "Expedient Synthesis of Triazole-Linked Glycosyl Amino Acids and Peptides," Org. Lett. 6 (18):3123-3216 (2004).
Li et al., "Design and Synthesis of a Template-assembled Oligomannose Cluster as an Epitope Mimic for Human HIV-Neutralizing Antibody 2G12," Org. Biomol. Chem. 2:483-488 (2004).

(Continued)

Primary Examiner — Jezia Riley
(74) Attorney, Agent, or Firm — LeClairRyan PLLC

(57) ABSTRACT

Described herein are oligosaccharide-oligonucleotide conjugates useful as vaccines against one or more human or veterinary therapeutic indications, and methods of synthesizing and identifying them. The conjugates may be identified using non-human antibodies as binding targets, thereby expanding the power and scope of the invention. Efficacious conjugates may be identified through an iterative screening process.

28 Claims, 21 Drawing Sheets

Specification includes a Sequence Listing.

(56) References Cited

OTHER PUBLICATIONS

MacPherson et al., "Multivalent Glycocluster Design Through Directed Evolution," Angew. Chem. Int. Ed. 50:11238-11242 (2011).
Meldal et al., "Cu-Catalyzed Azide-Alkyne Cycloaddition," Chem. Rev. 108(8):2952-3015 (2008).
Miller et al., "Synthesis of Fish Antifreeze Neoglycopeptides Using Microwave-Assisted "Click Chemistry"," Org. Lett. 11(11):2409-2412 (2009).
Ni et al., "Toward a Carbohydrate-Based HIV-1 Vaccine: Synthesis and Immunological Studies of Oligomannose-Containing Glycoconjugates," Bioconjugate Chem. 17(2):493-500 (2006).
Nyffeler et al., "The Chemistry of Amine-Azide Interconversion: Catalytic Diazotransfer and Regioselective Azide Reduction," J. Am. Chem. Soc. 124(36):10773-10778 (2002).
Wang et al., "Novel Template-Assembled Oligosaccharide Clusters as Epitope Mimics for HIV-Neutralizing Antibody 2G12. Design, Synthesis, and Antibody Binding Study," Org. Biornol. Chem. 5:1529-1540 (2007).
Wang et al., "Targeting the Carbohydrates on HIV-1: Interaction of Oligomannose Dendrons with Human Monoclonal Antibody 2G12 and DC-SIGN," PNAS 105(10):3690-3695 (2008).
Zhang et al., "Glycosylation Using a One-Electron-Transfer, Homogeneous Reagent. Application to an Efficient Synthesis of the Trimannosyl Core of N-glycosylproteins," Carbohydrate Research 236:73-88 (1992).
International Search Report dated Apr. 6, 2012, from PCT/US2011/039949.
Supplementary European Search Report dated Oct. 24, 2013, from EP11793228.

\* cited by examiner

Figure 1

| Oligonucleotide | Sequence |
|---|---|
| Hairpin library | 5' [CTGTTGTTCCGCAGTCACCTT]NNNNNNNNNNNNNNNNN<br>NNNNNNNNCCCGTACCCG_TATTTGGTGGCAAGGATGACAAGG_<br>_ATTTTATATTTTATATTTTTATTTTATTAT_CGGGTACGGG<br>[bracketed]=aptamerrev binding region<br>bold=stem region<br>_italics_=loop region<br>underlined=aptamerfor binding region<br>$N_{25}$=Randomized region |
| Regeneration primer | 5' biotin/CCCGTACCCGATAATAAAATAAAAATATAAAAT<br>ATAAAATCCTTGTCATCCTTGCCACCA |
| Aptamerfor | 5' [CCTTGTCATCCTTGCCACCA] |
| Aptamerfor-biotin | 5' biotin/[CCTTGTCATCCTTGCCACCA] |
| Aptamerrev | 5' [CTGTTGTTCCGCAGTCACCTT] |
| Aptamerrev-biotin | 5' biotin/[CTGTTGTTCCGCAGTCACCTT] |
| Hairpin primer | 5' CACCAAATACGGGTACGGG |

Figure 2

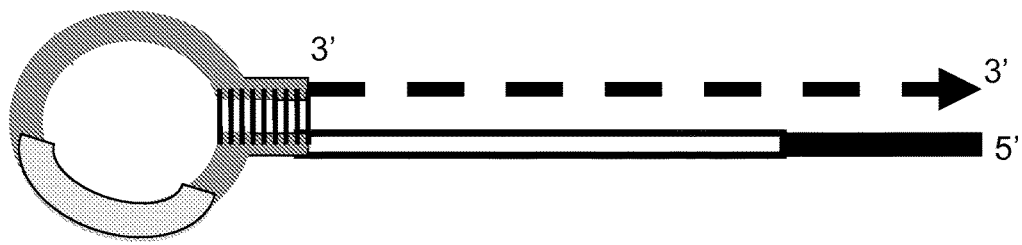

Figure 12

Sequences of clones, (+) strand, 5'->3':

1
CCTTGTCATCCTTGCCACCAAATACGGGTAAGGATGTTATAGATCAACGAATCATTAT [AAGGTGACTGCGGAACAACAG]
3
CCTTGTCATCCTTGCCACCAAATACGGGCCACGGCGCACGTCTCACCGCACTCTTAAGT [AAGGTGACTGCGGAACAACAG]
4/5
CCTTGTCATCCTTGCCACCAAATACGGGGACGCCTGTCATCCTGGTCATTACT [GAGGTGACTGCGGAACAACAG]
6
CCTTGTCATCCTTGCCACCAAATACGGGTGCGGGCGCGCTTTGTTTCAGCTCATGATAT [AAGGTGACTGCGGAACAACAG]
8
CCTTGTCATCCTTGCCACCAAATACGGGATACGGGTCGGTCATGATCATCAGTATGTCAT [AAGGTGACTGCGGAACAACAG]
9
CCTTGTCATCCTTGCCACCAAATACAGGTACGGGTCCATTATCGCGTGTCGTGTGCCGA [AAGGTGACTGCGGAACAACAG]
11
CCTTGTCATCCTTGCCACCAA-TACGGGTACGGAGGCCTTTCTCCATTGGGACGTCTC [AAGGTGACTGCGGAACAACAG]
13
CCTTGTCATCCTTGCCACCAAATACGGGTATGGGTTCGTTCATTCTCCTTACCATTGTC [AAGGTGACTGCGGAACAACAG]
14
CCTTGTCATCCTTGCCACCAAATACGGTACACGGGCAATTCAGAGCTCCATTGCGCTCT [AAGGTGACTGCGGAACAACAG]
15
CCTTGTCATCCTTGCCACCAA-TACGGGCACGGGCGTTTGTCTCATTACGTGCTAATC [AAGGTGACTGCGGAACAACAG]
16/23
CCTTGTCATCCTTGCCACCAATTACGGGTACGGGCCCGGCTGTTTCAGATGCTGTAAGT [AAGGTGACTGCGGAACAACAG]
18
CCTTGTCATCCTTGCCACCAAATACGGGTACGGGCCGCGGTGTCTCATCCGCATTTATA [AGGTGACTGCGGAACAACAG]
19
CCTTGTCATCCTTGCCACCAAATACGGGTACGGGCGCTTTGTCTATGGTGTCGTTGACT [AAGGTGACTGCGGAACAACAG]
21
CCTTGTCATCCTTGCCACCAAATACGGGTCAGCTCGTCTCCACCTGCTGTGTGT [AAGGTGACTGCGGAACAACAG]
22
CCTTGTCATCCTTGCCACCAAATAAGGGTACGGGCCATTGACCGCCATTGCCGATTCCA [AAGGTGACTGCGGAACAACAG]

Figure 16
(a)
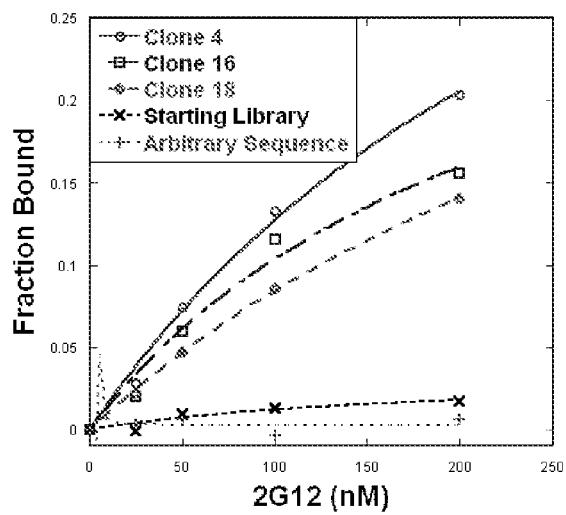
(b)
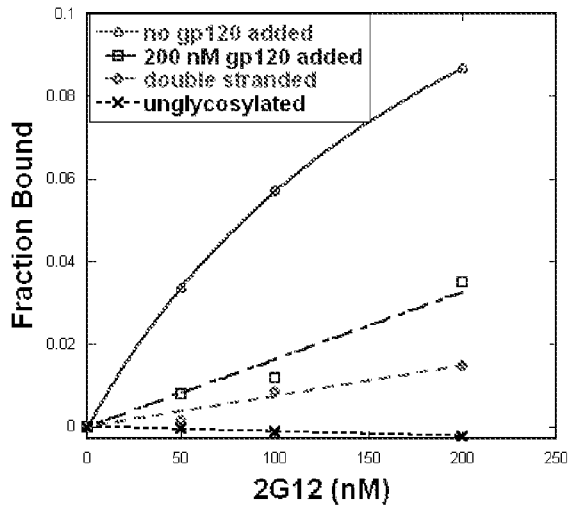

Figure 17

| | Sequence | $K_d$ (nM) | $F_{max}$ |
|---|---|---|---|
| 1 | CGGGTACGGGCCCGGCSGSSSCAGASGCSGSAAGSAAGGSGACSGCGGAACAACAG | 260 ± 60† | 0.34 ± 0.05 |
| 2 | TACGGGCCCGGCSGSSSCAGASGCSGSAAGSAAGGSGACSGCGGAACAACAG | 210 ± 40 | 0.25 ± 0.03 |
| 3 | CCCGGCTGTTTCAGASGCSGSAAGSAAGGSGACSGCGGAACAACAG | n.b. | n.b. |
| 4 | CGGGTACGGGCCCGGCSGSSSCAGASGCSGSAAGSAAGGSGACSGC | 120 ± 80 | 0.19 ± 0.06 |
| 5 | TACGGGCCCGGCSGSSSCAGASGCSGSAAGSAAGGSGACSGC | >> 200 | 1** |
| 6 | CCCGGCTGTTTCAGASGCSGSAAGSAAGGSGACSGC | n.b. | n.b. |
| 7 | TACGGGCCCGGCSGSSSCAGASGCSGSAAGSAA | n.b. | n.b. |
| 8 | CCCGGCTGTTTCAGASGCSGSAAGSAA | n.b. | n.b. |
| 9* | CGGGTACGGGCCCGGCSGSSSCAGASGCSGSAAGSAAGGSGACSGCGGAACAACAG | 500 ± 90 | 0.28 ±0.03 |
| 10* | CGGGTACGGGCCCGGCGGSSSCAGASGCSGSAAGSAAGGSGACSGCGGAACAACAG | 550 ± 240 | 0.33 ± 0.08 |
| 11* | CGGGTACGGGCCCGGCSGGSSCAGASGCSGSAAGSAAGGSGACSGCGGAACAACAG | >> 800 | 1** |
| 12* | CGGGTACGGGCCCGGCSGSGSCAGASGCSGSAAGSAAGGSGACSGCGGAACAACAG | 490 ± 130 | 0.49 ± 0.07 |
| 13* | CGGGTACGGGCCCGGCSGSSGCAGASGCSGSAAGSAAGGSGACSGCGGAACAACAG | >> 800 | 1** |
| 14* | CGGGTACGGGCCCGGCSGSSSCAGAGGCSGSAAGSAAGGSGACSGCGGAACAACAG | 310 ± 40 | 0.21 ± 0.01 |
| 15* | CGGGTACGGGCCCGGCSGSSSCAGASGCGGSAAGSAAGGSGACSGCGGAACAACAG | 510 ± 90 | 0.34± 0.03 |
| 16* | CGGGTACGGGCCCGGCSGSSSCAGASGCSGAAGSAAGGSGACSGCGGAACAACAG | 570 ± 80 | 0.42 ± 0.05 |
| 17* | CGGGTACGGGCCCGGCSGSSSCAGASGCSGSAAGGAAGGSGACSGCGGAACAACAG | 1800 ± 300 | 0.50 ± 0.08 |
| 18* | CGGGTACGGGCCCGGCSGSSSCAGASGCSGSAAGSAAGGGACSGCGGAACAACAG | 710 ± 180 | 0.27 ± 0.04 |
| 19* | CGGGTACGGGCCCGGCSGSSSCAGASGCSGSAAGSAAGGSGACGGCGGAACAACAG | >> 800 | 1** |
| 20* | CGGGTACGGGCCCGGCGGSGSCAGAGGCGGGAAGGAAGGGACSGCGGAACAACAG | n.b. | n.b. |
| 21* | CGGGTACGGGCCCGGCUGSUSCAGAUGCUGUAAGUAAGGUGACSGCGGAACAACAG | n.b. | n.b. |

Figure 21
(a)
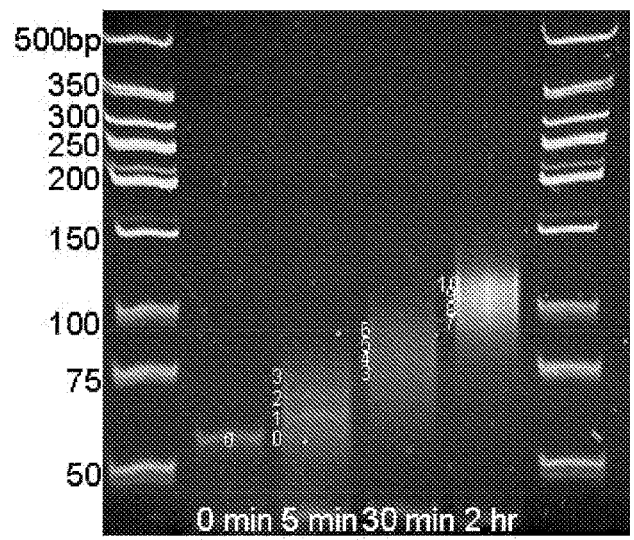
(b)
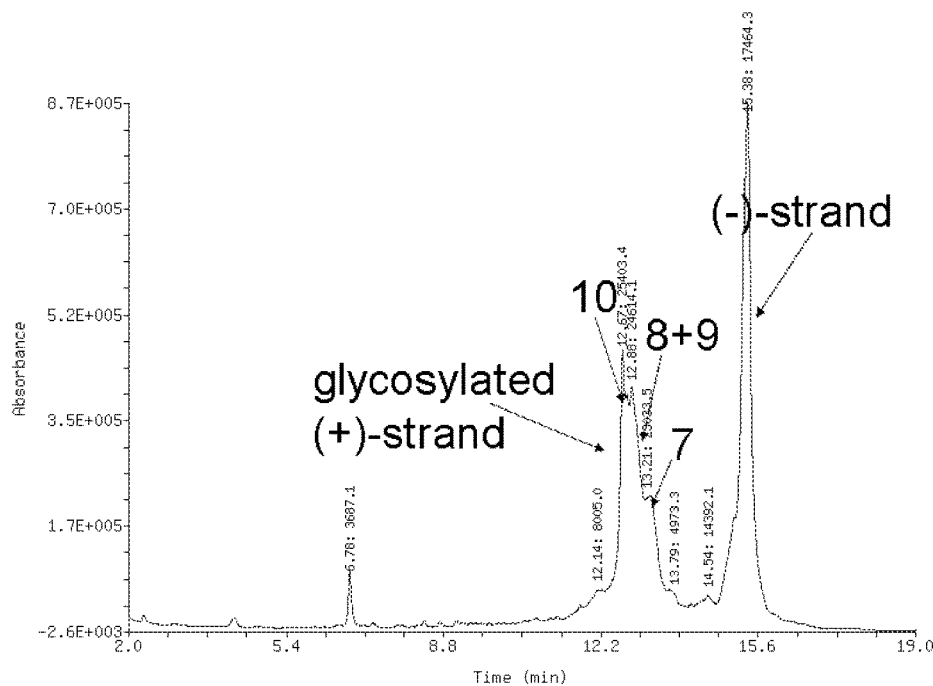

Figure 22

| RT (min) | Target Mass (Da) | Observed Mass (Da) | Mass Error | LC/MS Area Percent | Identity |
|---|---|---|---|---|---|
| 12.66 | 25407.5 | 25403.4 | -4.1 Da (-0.016 %) | 19.15 | (click 10x) |
| 12.87 | 24617.8 | 24614.1 | -3.7 Da (-0.015 %) | 22.60 | (click 9x) |
| 12.87 | 23828.0 | 23824.6 | -3.4 Da (-0.014 %) | 9.16 | (click 8x) |
| 13.20 | 23038.3 | 23033.5 | -4.8 Da (-0.021 %) | 0.36 | (click 7x) |
| 15.37 | 17465.5 | 17464.3 | -1.2 Da (-0.007 %) | 46.25 | (-)-strand |

Figure 23

| Time (min.) | MeOH (%) | $H_2O$ (%) | Flow Rate (mL/min.) |
|---|---|---|---|
| 0 | 1 | 99 | 4 |
| 6 | 1 | 99 | 4 |
| 6.5 | 1 | 99 | 3 |
| 16 | 60 | 40 | 3 |
| 60 | 60 | 40 | 3 |

Figure 24
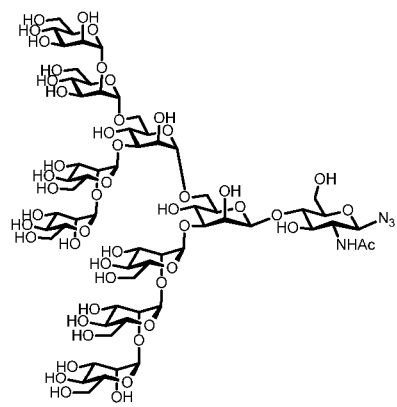
XIII
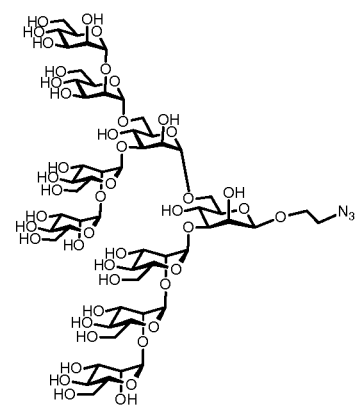
XIV

SEQUENCE LISTING

<160> NUMBER OF SEQ ID NOS: 43

<210> SEQ ID NO 1
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

```
<221> NAME/KEY: modified_base
<222> LOCATION: (22)..(46)
<223> OTHER INFORMATION: a, c, t, g, unknown or other

<400> SEQUENCE: 1
ctgttgttcc gcagtcacct tnnnnnnnnn nnnnnnnnnn nnnnnccccg tacccgtatt      60
tggtggcaag gatgacaagg attttatatt ttatattttt attttattat cgggtacggg    120

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-Biotin

<400> SEQUENCE: 2
cccgtacccg ataataaaat aaaaatataa aatataaaat ccttgtcatc cttgccacca     60

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccttgtcatc cttgccacca                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Biotin

<400> SEQUENCE: 4
ccttgtcatc cttgccacca                                                 20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctgttgttcc gcagtcacct t                                               21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Biotin

<400> SEQUENCE: 6
```
ctgttgttcc gcagtcacct t                                                 21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccaaatac gggtacggg                                                    19

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccttgtcatc cttgccacca aatacgggta aggatgttat aagatcaacg aatcattata      60
aggtgactgc ggaacaacag                                                  80

<210> SEQ ID NO 9
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccttgtcatc cttgccacca aatacggcca cgggcgcacg tctcaccgca ctcttaagta      60
aggtgactgc ggaacaacag                                                  80

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccttgtcatc cttgccacca aatacgcgta cggggacgcc tgtcatcctg gtcattactg      60
aggtgactgc ggaacaacag                                                  80

<210> SEQ ID NO 11
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccttgtcatc cttgccacca aatacgggtg cgggcgcgct tgtttcagc tcatgatata       60 aggtgactgc ggaacaacag                                                  80

<210> SEQ ID NO 12
<211> LENGTH: 80
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 12
ccttgtcatc cttgccacca aatacggata cgggtcggtc atgatcatca gtatgtcata    60
aggtgactgc ggaacaacag                                                80

<210> SEQ ID NO 13
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccttgtcatc cttgccacca aatacaggta cgggtccatt atcgcgtgtc gtgtgccgaa    60
aggtgactgc ggaacaacag                                                80

<210> SEQ ID NO 14
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccttgtcatc cttgccacca atacgggtac gggaggcctt tctccattgg gacgtctcaa    60
ggtgactgcg gaacaacag                                                 79

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ccttgtcatc cttgccacca aatacgggta tgggttcgtt cattctcctt accattgtca    60
aggtgactgc ggaacaacag                                                80

<210> SEQ ID NO 16
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccttgtcatc cttgccacca aatacgtaca cggggcaatt cagagctcca ttgcgctcta    60
aggtgactgc ggaacaacag                                                80

<210> SEQ ID NO 17
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
ccttgtcatc cttgccacca atacgggcac ggggcgtttg tctcattacg tgctaatcaa      60
ggtgactgcg gaacaacag                                                  79

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccttgtcatc cttgccacca attacgggta cgggcccggc tgtttcagat gctgtaagta      60
aggtgactgc ggaacaacag                                                 80

<210> SEQ ID NO 19
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccttgtcatc cttgccacca aatacgggta cgggccgcgg tgtctcatcc gcatttataa      60
ggtgactgcg gaacaacag                                                  79

<210> SEQ ID NO 20
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccttgtcatc cttgccacca aatacgggta cgggcgcttt gtcgctatgg tcgttgacta      60
aggtgactgc ggaacaacag                                                 80

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccttgtcatc cttgccacca aatacgggta cgggtcagct cgtctcacct gctgtgtgta      60
aggtgactgc ggaacaacag                                                 80

<210> SEQ ID NO 22
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccttgtcatc cttgccacca aataagggta cgggccattg accgccattg ccgattccaa      60
```
aggtgactgc ggaacaacag                                                  80

<210> SEQ ID NO 23
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 23
cgggtacggg cccggcuguu ucagaugcug uaaguaaggu gacugcggaa caacag         56

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Man4-glycosylated 5-ethynyl-deoxyuridine
<220> FEATURE:
<221> NAME/KEY: modified_base
<222> LOCATION: (15)..(17)
<223> OTHER INFORMATION: Man4-glycosylated 5-ethynyl-deoxyuridine
<220> FEATURE:
<221> NAME/KEY: modified_base
<222> LOCATION: (22)..(22)
<223> OTHER INFORMATION: Man4-glycosylated 5-ethynyl-deoxyuridine
<220> FEATURE:
<221> NAME/KEY: modified_base
<222> LOCATION: (25)..(25)
<223> OTHER INFORMATION: Man4-glycosylated 5-ethynyl-deoxyuridine
<220> FEATURE:

<221> NAME/KEY: modified_base
<222> LOCATION: (27)..(27)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (36)..(36)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine

<400> SEQUENCE: 24
tacgggcccg gcuguuucag augcuguaag uaaggugacu gcggaacaac ag        52

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: Man4-glycosylated 5-ethynyl-deoxyuridine
<220> FEATURE:
<221> NAME/KEY: modified_base
<222> LOCATION: (19)..(19)
<223> OTHER INFORMATION: Man4-glycosylated 5-ethynyl-deoxyuridine
<220> FEATURE:
<221> NAME/KEY: modified_base
<222> LOCATION: (21)..(21)
<223> OTHER INFORMATION: Man4-glycosylated 5-ethynyl-deoxyuridine
<220> FEATURE:
<221> NAME/KEY: modified_base
<222> LOCATION: (25)..(25)
<223> OTHER INFORMATION: Man4-glycosylated 5-ethynyl-deoxyuridine
<220> FEATURE:
<221> NAME/KEY: modified_base
<222> LOCATION: (30)..(30)
<223> OTHER INFORMATION: Man4-glycosylated 5-ethynyl-deoxyuridine
<220> FEATURE:
<221> NAME/KEY: modified_base
<222> LOCATION: (34)..(34)
<223> OTHER INFORMATION: Man4-glycosylated 5-ethynyl-deoxyuridine

<400> SEQUENCE: 25
cccggctgtt tcagaugcug uaaguaaggu gacugcggaa caacag        46

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine

```
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 26
cgggtacggg cccggcuguu ucagaugcug uaaguaaggu gacugc                    46

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Man4-glycosylated 5-ethynyl-deoxyuridine
<220> FEATURE:
<221> NAME/KEY: modified_base
<222> LOCATION: (15)..(17)
<223> OTHER INFORMATION: Man4-glycosylated 5-ethynyl-deoxyuridine
<220> FEATURE:
<221> NAME/KEY: modified_base
<222> LOCATION: (22)..(22)
<223> OTHER INFORMATION: Man4-glycosylated 5-ethynyl-deoxyuridine
<220> FEATURE:
<221> NAME/KEY: modified_base
<222> LOCATION: (25)..(25)
<223> OTHER INFORMATION: Man4-glycosylated 5-ethynyl-deoxyuridine
<220> FEATURE:
<221> NAME/KEY: modified_base
<222> LOCATION: (27)..(27)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (36)..(36)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine

<400> SEQUENCE: 27
tacgggcccg gcuguuucag augcuguaag uaaggugacu gc                        42

<210> SEQ ID NO 28
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: Man4-glycosylated 5-ethynyl-deoxyuridine
<220> FEATURE:
<221> NAME/KEY: modified_base
<222> LOCATION: (19)..(19)
<223> OTHER INFORMATION: Man4-glycosylated 5-ethynyl-deoxyuridine
<220> FEATURE:
<221> NAME/KEY: modified_base
<222> LOCATION: (21)..(21)
<223> OTHER INFORMATION: Man4-glycosylated 5-ethynyl-deoxyuridine
<220> FEATURE:
<221> NAME/KEY: modified_base
<222> LOCATION: (25)..(25)
<223> OTHER INFORMATION: Man4-glycosylated 5-ethynyl-deoxyuridine
<220> FEATURE:
<221> NAME/KEY: modified_base
<222> LOCATION: (30)..(30)
<223> OTHER INFORMATION: Man4-glycosylated 5-ethynyl-deoxyuridine
<220> FEATURE:
<221> NAME/KEY: modified_base
<222> LOCATION: (34)..(34)
<223> OTHER INFORMATION: Man4-glycosylated 5-ethynyl-deoxyuridine

<400> SEQUENCE: 28
cccggctgtt tcagaugcug uaaguaaggu gacugc                                 36

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(13)
<223> OTHER INFORMATION: Man4-glycosylated 5-ethynyl-deoxyuridine
<220> FEATURE:
<221> NAME/KEY: modified_base
<222> LOCATION: (15)..(17)
<223> OTHER INFORMATION: Man4-glycosylated 5-ethynyl-deoxyuridine
<220> FEATURE:
<221> NAME/KEY: modified_base
<222> LOCATION: (22)..(22)
<223> OTHER INFORMATION: Man4-glycosylated 5-ethynyl-deoxyuridine
<220> FEATURE:
<221> NAME/KEY: modified_base
<222> LOCATION: (25)..(25)
<223> OTHER INFORMATION: Man4-glycosylated 5-ethynyl-deoxyuridine
<220> FEATURE:
<221> NAME/KEY: modified_base
<222> LOCATION: (27)..(27)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine

<400> SEQUENCE: 29
tacgggcccg gcuguuucag augcuguaag uaa                                    33
```

```
<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(16)
<223> OTHER INFORMATION: Man4-glycosylated 5-ethynyl-deoxyuridine
<220> FEATURE:
<221> NAME/KEY: modified_base
<222> LOCATION: (19)..(19)
<223> OTHER INFORMATION: Man4-glycosylated 5-ethynyl-deoxyuridine
<220> FEATURE:
<221> NAME/KEY: modified_base
<222> LOCATION: (21)..(21)
<223> OTHER INFORMATION: Man4-glycosylated 5-ethynyl-deoxyuridine
<220> FEATURE:
<221> NAME/KEY: modified_base
<222> LOCATION: (25)..(25)
<223> OTHER INFORMATION: Man4-glycosylated 5-ethynyl-deoxyuridine

<400> SEQUENCE: 30
cccggctgtt tcagaugcug uaaguaa                                           27

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 31
cgggtacggg cccggcuguu ucagaugcug uaaguaaggu gacugcggaa caacag          56
```

```
<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 32
cgggtacggg cccggcgguu ucagaugcug uaaguaaggu gacugcggaa caacag      56

<210> SEQ ID NO 33
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (20)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
```

-continued

```
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 33
cgggtacggg cccggcuggu ucagaugcug uaaguaaggu gacugcggaa caacag      56

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(19)
<223> OTHER INFORMATION: Man4-glycosylated 5-ethynyl-deoxyuridine
<220> FEATURE:
<221> NAME/KEY: modified_base
<222> LOCATION: (21)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 34
cgggtacggg cccggcugug ucagaugcug uaaguaaggu gacugcggaa caacag      56

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
```

```
<223> OTHER INFORMATION: Man4-glycosylated 5-ethynyl-deoxyuridine
<220> FEATURE:
<221> NAME/KEY: modified_base
<222> LOCATION: (19)..(20)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 35
cgggtacggg cccggcuguu gcagaugcug uaaguaaggu gacugcggaa caacag      56

<210> SEQ ID NO 36
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 36
cgggtacggg cccggcuguu ucagaggcug uaaguaaggu gacugcggaa caacag      56
```

```
<210> SEQ ID NO 37
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 37
cgggtacggg cccggcuguu ucagaugcgg uaaguaaggu gacugcggaa caacag        56

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
```

```
<221> NAME/KEY: modified_base
<222> LOCATION: (44)..(44)
<223> OTHER INFORMATION: Man4-glycosylated 5-ethynyl-deoxyuridine

<400> SEQUENCE: 38
cgggtacggg cccggcuguu ucagaugcug gaaguaaggu gacugcggaa caacag      56

<210> SEQ ID NO 39
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 39
cgggtacggg cccggcuguu ucagaugcug uaaggaaggu gacugcggaa caacag      56

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
```

```
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 40
cgggtacggg cccggcuguu ucagaugcug uaaguaaggg gacugcggaa caacag      56

<210> SEQ ID NO 41
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: Man4-glycosylated 5-ethynyl-deoxyuridine
<220> FEATURE:
<221> NAME/KEY: modified_base
<222> LOCATION: (19)..(21)
<223> OTHER INFORMATION: Man4-glycosylated 5-ethynyl-deoxyuridine
<220> FEATURE:
<221> NAME/KEY: modified_base
<222> LOCATION: (26)..(26)
<223> OTHER INFORMATION: Man4-glycosylated 5-ethynyl-deoxyuridine
<220> FEATURE:
<221> NAME/KEY: modified_base
<222> LOCATION: (29)..(29)
<223> OTHER INFORMATION: Man4-glycosylated 5-ethynyl-deoxyuridine
<220> FEATURE:
<221> NAME/KEY: modified_base
<222> LOCATION: (31)..(31)
<223> OTHER INFORMATION: Man4-glycosylated 5-ethynyl-deoxyuridine
<220> FEATURE:
<221> NAME/KEY: modified_base
<222> LOCATION: (35)..(35)
<223> OTHER INFORMATION: Man4-glycosylated 5-ethynyl-deoxyuridine
<220> FEATURE:
<221> NAME/KEY: modified_base
<222> LOCATION: (40)..(40)
<223> OTHER INFORMATION: Man4-glycosylated 5-ethynyl-deoxyuridine

<400> SEQUENCE: 41
cgggtacggg cccggcuguu ucagaugcug uaaguaaggu gacggcggaa caacag      56

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: Man4-glycosylated 5-ethynyl-deoxyuridine
<220> FEATURE:
<221> NAME/KEY: modified_base
<222> LOCATION: (21)..(21)
```

```
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 42
cgggtacggg cccggcggug ucagaggcgg gaaggaaggg gacugcggaa caacag      56

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (19)..(19)
<223> OTHER INFORMATION: Man4-glycosylated 5-ethynyl-deoxyuridine
<220> FEATURE:
<221> NAME/KEY: modified_base
<222> LOCATION: (21)..(21)
<223> OTHER INFORMATION: Man4-glycosylated 5-ethynyl-deoxyuridine
<220> FEATURE:
<221> NAME/KEY: modified_base
<222> LOCATION: (44)..(44)
<223> OTHER INFORMATION: Man4-glycosylated 5-ethynyl-deoxyuridine

<400> SEQUENCE: 43
cgggtacggg cccggcuguu ucagaugcug uaaguaaggu gacugcggaa caacag      56
```

METHODS FOR THE DEVELOPMENT OF VACCINES BASED ON OLIGOSACCHARIDE-OLIGONUCLEOTIDE CONJUGATES

RELATED APPLICATIONS

This application is a continuation of U.S. patent application Ser. No. 13/701,849, which is a national stage application under 35 U.S.C. § 371 from PCT Application No. PCT/US11/039949, filed Jun. 10, 2011, which claims the benefit of priority to U.S. Provisional Patent Application Ser. No. 61/353,857, filed Jun. 11, 2010, the contents of which are hereby incorporated by reference.

GOVERNMENT SUPPORT

This invention was made with government support under Grant Nos. R01 GM054403, U01 AI075466, and R01 AI090745, awarded by the National Institutes of Health. The government has certain rights in the invention.

BACKGROUND OF THE INVENTION

Certain monoclonal antibodies have therapeutic potential against a particular disease, even though similar antibodies seldom or never arise during disease progression in most humans. For example, in models of HIV infection antibody 2G12 is known to neutralize a broad range of HIV strains and protect rhesus macaques, but 2G12-like antibodies are rarely produced in HIV-positive humans. In such cases, a "reverse immunology" approach would be desirable, in which an immunogen is designed which structurally mimics the epitope of the therapeutically useful monoclonal antibody. Immunization with this epitope mimic would then elicit an antibody response mimicking the monoclonal antibody.

The success of this strategy depends on the extent to which one can design a molecule that is a good structural and conformational mimic of the native epitope. This goal requires a good structural or conformational understanding of the epitope structure. "Carbohydrate epitopes" are epitopes in which a carbohydrate is a necessary component for antibody binding. However, the antibody-epitope binding interaction is rarely understood at the atomic structural level and, in most cases, it is not known whether the antibody binds to structural features neighboring the carbohydrate in addition to the carbohydrate itself. Moreover, carbohydrates are flexible and may exhibit different conformational profiles when attached to structures other than those present in the actual target protein.

For example, the majority of HIV vaccine approaches to date have tested either HIV protein subunits or peptides, and/or caused the host to make these proteins by intracellular delivery of HIV DNA using viral vectors or gold particles. Because a broadly-neutralizing antibody, 2G12, binds to a cluster of carbohydrates on the viral envelope protein gp120, a few groups have designed and tested synthetically clustered carbohydrate immunogens in an attempt to mimic the 2G12 epitope and thus elicit 2G12-like antibodies. In these approaches, the backbones linking the carbohydrates were flexible organic chains or cyclic peptides that were easy to synthesize. No study has described an attempt to mimic in an exact way the natural backbone in which the carbohydrates are embedded. The choice of backbone is key; due to the flexibility of carbohydrates, their conformation, spacing, and orientation is undoubtedly influenced by the surfaces they are embedded within, and the flexible carbohydrate cluster immunogens designed to date have not achieved true conformational mimicry of the epitope. The choice of backbone is also important because the peptide structures of gp120 in which the carbohydrates are embedded are likely make some contact with 2G12 and comprise part of the epitope.

Further, other important information regarding 2G12 binding to HIV remains unknown, including: precisely which oligomannans on the gp120 surface are bound by the antibody; whether the antibody also binds to polypeptide surface residues; and how the oligomannans are conformationally supported by the protein. Synthetic clusters of oligomannans mounted on non-natural designed scaffolds have so far failed to elicit 2G12-like antibodies, possibly because such epitope mimics do not adequately resemble the native epitope. Even with perfect structural knowledge of an epitope, a priori design of antigens that faithfully mimic its structure is currently impossible.

Additionally, a major limitation of RNA and DNA aptamers is that the nucleotide building blocks are limited to the naturally occurring bases and close analogues that act as substrates for DNA or RNA polymerases. The utility of the oligonucleotide framework, and the power of the selection process, could be greatly extended if the bases could be more extensively modified.

SUMMARY OF THE INVENTION

In certain embodiments, the invention relates to a method, comprising the steps of:
  (a) combining a plurality of oligonucleotides, a first DNA polymerase, and a plurality of deoxyribonucleotide triphosphates, wherein
    the oligonucleotides comprise a first primer binding site on the 5' end, a randomized region, and a stem-loop region;
    the randomized region is located between the first primer binding site and the stem-loop region;
    the stem-loop region comprises a second primer binding site; and at least one of the deoxyribonucleotide triphosphates comprises a reactive substituent;
  thereby forming a plurality of extended oligonucleotides comprising an original strand and an extended strand, wherein the extended strand comprises at least one reactive substituent;
  (b) combining a plurality of modifying compounds and the plurality of extended oligonucleotides under reaction conditions,
  thereby forming a plurality of modified extended oligonucleotides comprising the original strand and a modified extended strand; and
  (c) combining a plurality of primers complementary to the second primer binding site, a second DNA polymerase, the plurality of modified extended oligonucleotides, and a plurality of deoxyribonucleotide triphosphates
  thereby creating duplexes with the original strands and displacing the modified extended strands.

In certain embodiments, the invention relates to a method, comprising the steps of
  (a) combining a plurality of oligonucleotides, a first DNA polymerase, and a plurality of deoxyribonucleotide triphosphates,
    wherein
    the oligonucleotides comprise a first primer binding site on the 5' end, a randomized region, and a stem-loop region;

the randomized region is located between the first primer binding site and the stem-loop region;

the stem-loop region comprises a second primer binding site; and at least one of the deoxyribonucleotide triphosphates comprises a reactive substituent;

thereby forming a plurality of extended oligonucleotides comprising an original strand and an extended strand, wherein the extended strand comprises at least one reactive substituent;

(b) combining a plurality of modifying compounds and the plurality of extended oligonucleotides under reaction conditions, thereby forming a plurality of modified extended oligonucleotides comprising the original strand and a modified extended strand;

(c) combining a plurality of primers complementary to the second primer binding site, a second DNA polymerase, the plurality of modified extended oligonucleotides, and a plurality of deoxyribonucleotide triphosphates thereby creating duplexes with the original strands, displacing the modified extended strands, and forming a plurality of modified single-stranded oligonucleotides;

(d) combining the plurality of modified single-stranded oligonucleotides and a target protein;

(e) isolating the modified single-stranded oligonucleotides that bind to the target protein, thereby identifying a plurality of selected oligonucleotides;

(f) amplifying the plurality of selected oligonucleotides, thereby forming a plurality of complementary oligonucleotides; and (g) preparing a plurality of regenerated selected oligonucleotides from the plurality of complementary oligonucleotides.

In certain embodiments, the invention relates to an oligonucleotide, wherein the oligonucleotide comprises at least one non-natural deoxynucleoside; and the non-natural deoxynucleoside comprises an oligosaccharide moiety and a triazole moiety.

BRIEF DESCRIPTION OF THE FIGURES

FIG. 1 depicts an original oligonucleotide library with a primer binding site on the 5' end, followed by a randomized region (~25 bases) followed by a stem-loop region containing a second primer binding site. FIG. 1 discloses SEQ ID NOS 1-7, respectively, in order of appearance.

FIG. 2 depicts a schematic representation of an extended hairpin product containing ethynyl deoxyuridine (EDU) (an extended oligonucleotide comprising an original strand and an extended strand). Polymerase extension with 5-ethynyl-deoxyuridine triphosphate (EDUTP) instead of thymidine triphosphate allows for the incorporation of a moiety with a reactive substituent that can be modified using "click chemistry."

FIG. 12 depicts the sequences of clones, (+)-strand, from 5' end to 3'end (left to right) (italicized=loop region; bold=stem region; [bracketed]=aptamerrev binding region). FIG. 12 discloses SEQ ID NOS 8-22, respectively, in order of appearance.

FIG. 16 depicts the results from the selection process. (a) Preliminary selection results: 2G12-dependent filter binding of clones 4, 16 and 18, the starting library, and arbitrary sequence containing 10 glycosylation sites. (b) Effects of glycosylation, gp120 competition, and single/double-strandedness on 2G12 binding by clone 16 determined by filter binding.

FIG. 17 depicts a mutagenesis study: Values of $K_d$ and fraction bound ($F_{max}$) for truncated and mutated clone 16. Entry 1 is unmutated clone 16. Underlined sequence is the random region. S is Man$_4$-glycosylated EdU. *The value of $K_d$ reported in the text, in entries 1-8 and entries 9-21 were measured with different batches of 2G12, giving slightly different values of $K_d$ for the parent clone 16 (text vs. entries 1 vs. 9). The $K_d$ values in entries 10-21 should be compared only with entry 9. **$K_d$ was much greater than the maximum 2G12 concentration tested and $F_{max}$ was constrained to 1 to fit curve with finite $K_d$ value. †Errors reported are the standard error of the curve fit in all cases except entry 1, for which the average of errors in entries 1-8 is reported. FIG. 17 discloses SEQ ID NOS 23-43, respectively, in order of appearance.

FIG. 21 depicts (a) PAGE of click reaction aliquots; and (b) RP-HPLC/ESI-MS chromatogram after 2 h.

FIG. 22 tabulates masses and abundances of observed species in the chromatogram from FIG. 21b.

FIG. 23 tabulates the HPLC gradient used in the purification of 5.

FIG. 24 depicts additional oligosaccharide-azide compounds (XIII and XIV) of the invention.

DETAILED DESCRIPTION OF THE INVENTION

Overview

Figure 3:
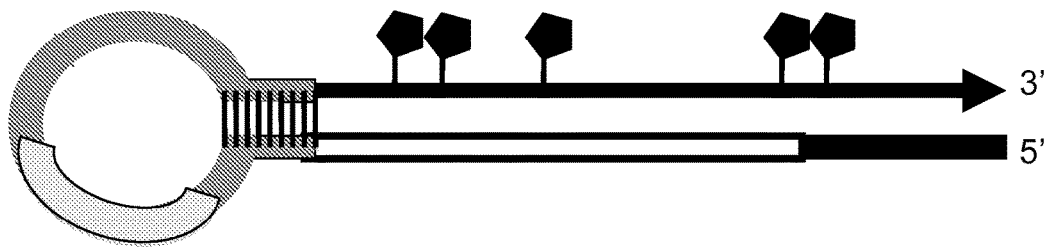
FIG. 3 depicts a schematic representation of a "clicked" hairpin (a modified extended oligonucleotide comprising an original strand and a modified extended strand). The extended hairpin product is purified and subsequently modified by "click chemistry." In this case, an azido sugar (a "modifying compound") reacts with the pendant ethynyl group (a "reactive substituent") to form a triazole in a copper-catalyzed reaction. This chemistry is robust and should be applicable to any azide.
Figure 4:
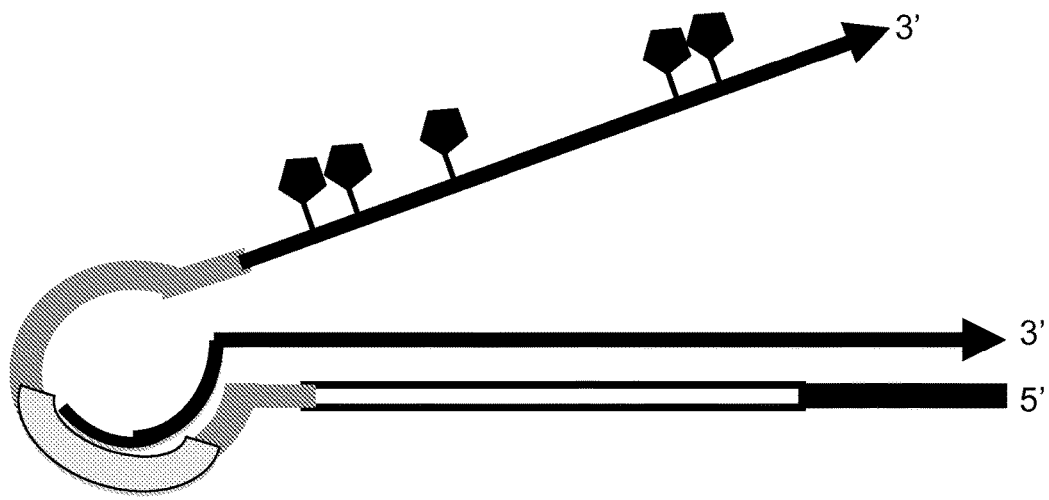
FIG. 4 depicts the displacement of the modified extended strand by providing a primer complementary to the primer binding site, creating a duplex with the naturally occurring nucleotides.
Figure 5:
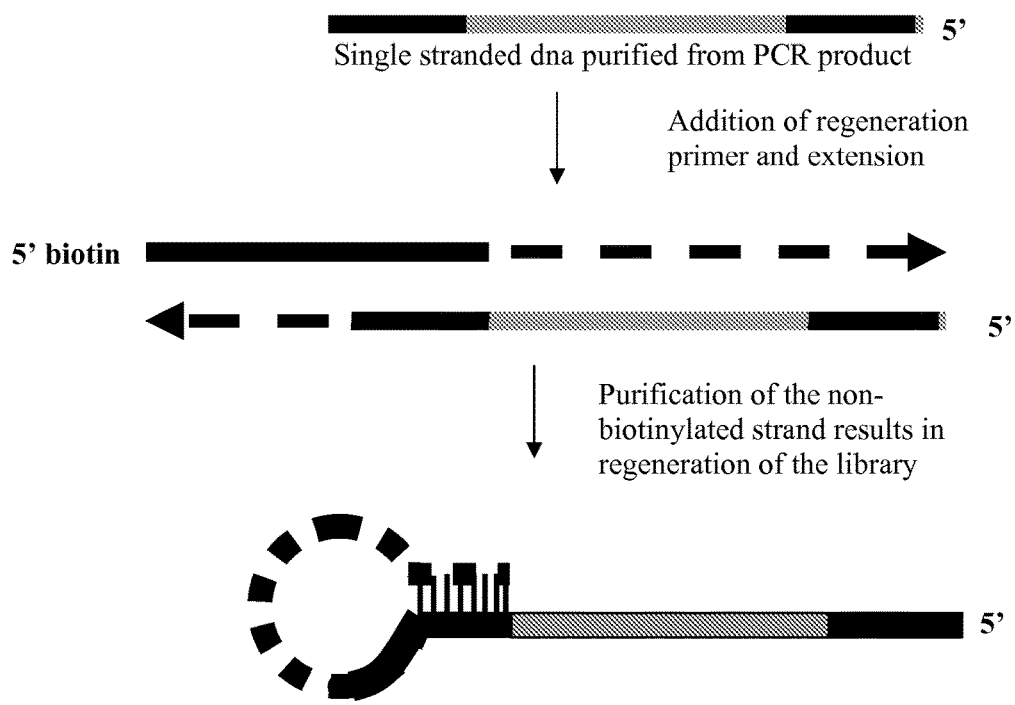
FIG. 5 depicts regeneration of the hairpin. Modified oligonucleotides that bind to a target protein, in this case the monoclonal antibody 2G12, may be isolated and amplified via PCR using primers aptamerfor-biotin and aptamerrev. Purification of the non-biotinylated strand and an additional extension using the biotinylated regeneration primer, followed by purification of the non-biotinylated extended product regenerates the hairpin as shown. Iterative rounds of selection and amplification will enrich the pool of modified oligonucleotides that bind to the target. The PCR product can be cloned and sequenced to identify the modified oligonucleotides that bind to the target. This procedure was used to construct a library of mannose-modified oligonucleotides, and identify modified oligonucleotides that bind to MAb 2G12.

One aspect of the invention relates to a method of directed evolution of carbohydrate-oligonucleotide conjugates. In certain embodiments, a large library of carbohydrate-modified oligonucleotides structures is synthesized, and then a therapeutically-useful monoclonal antibody is used to bind those members of the library which best resemble its native epitope. In certain embodiments, PCR enables amplification or diversification of the best binders from the first library, and the best epitope mimics are selected from subsequent library generations to provide improved binders. In certain embodiments, the carbohydrate-oligonucleotide conjugates obtained from the process present carbohydrates in an environment similar to that of the natural epitope, containing the optimal number of oligosaccharides, with the optimal spacing and conformation, and surrounded by oligonucleotide structures which mimic any necessary peptide component of the natural epitope. In certain embodiments, such a compound, when formulated with the appropriate immunogenic carrier and adjuvant, would constitute a vaccine.

In certain embodiments, the invention relates to a method of preparing and identifying a vaccine against a disease for which therapeutically-useful antibodies are known to bind to a carbohydrate structure. In certain embodiments, DNA is used as a backbone for carbohydrate vaccines. In certain embodiments, the disease is HIV/AIDS. In certain embodiments, the therapeutically-useful antibody is 2G12. In certain embodiments, the disease is cancer. In certain embodiments, the therapeutically-useful antibody recognizes a cancer antigen. In certain embodiments, the therapeutically-useful antibody is RAV12.

In certain embodiments, the invention relates to a method of preparing and identifying oligosaccharide-oligonucleotide conjugates which selectively disrupt a physiological glycoprotein-glycoprotein or protein-glycoprotein interaction in which the interaction involves pendant carbohydrate moieties of one or both of the participants.

In certain embodiments, the invention relates to a method of designing and identifying a novel carbohydrate cluster antigen by attaching carbohydrates to a library of DNA backbones and performing aptamer selection with 2G12. In certain embodiments, the invention relates to a method of designing and identifying glyco-DNAs in which the backbone clusters the carbohydrates in the optimal manner. As opposed to the numerous DNA vaccine approaches, in which DNA is delivered via viral vectors or gold particles and merely codes for a protein antigen, it is important to clarify that, in certain embodiments, the inventive glyco-DNA will be injected as a free molecule in μg quantities, because it is itself the antigen. In certain embodiments, the glyco-DNA fulfills three roles: 1) to orient optimally the attached carbohydrates in a position that mimics their presentation in the true 2G12 epitope, 2) to mimic structurally any possible peptide residues within the 2G12 epitope, and 3) to serve as a built-in adjuvant. In certain embodiments, the functioning of the glyco-DNA as a built-in adjuvant is in contrast with other carbohydrate vaccine approaches, where the carbohydrates were conjugated to proteins or peptides, and mostly failed to elicit anti-carbohydrate antibodies.

In certain embodiments, the invention relates to a method of eliciting a 2G12-like polyclonal antibody response. Given that monoclonal 2G12 antibody neutralizes a broad-range of HIV-1 strains and has a demonstrated protective effect in non-human primate models of HIV infection, there is good reason to believe that a 2G12-like polyclonal antibody response would also be protective. In certain embodiments, to elicit a 2G12-like response, two challenges must be overcome: 1) to develop an immunogen which structurally and conformationally mimics the 2G12 epitope, and 2) to overcome the poor immunogenicity of the carbohydrate epitope. In certain embodiments, the first challenge is addressed in the inventive methods by using 2G12 to select the best design of carbohydrate cluster from among trillions of possibilities. In certain embodiments, the second challenge is addressed in the inventive methods because the vaccine contains a DNA backbone. DNA is known to be a potent adjuvant, activating numerous Toll receptor pathways.

In certain embodiments, a method begins with a library of single-stranded DNA hairpins, wherein the 3' end of each hairpin is a primer for transcription across the randomized DNA template region of the hairpin. In certain embodiments, a primer annealed to the loop region of the hairpin initiates strand displacement-synthesis, thereby (1) liberating the transcribed strand to allow folding, and (2) linearizing the DNA template by making it double-stranded.

$Man_9GlcNAc_2$ oligosaccharides present in the 2G12 epitope of HIV surface protein gp120 have been synthesized. The structures of potentially desirable compounds may be simplified by substituting for the two GlcNAc residues a simple cyclohexyl linker bearing an azide (FIG. 7). FIG. 8 depicts the synthesis of $Man_4$-cyclohexyl azide (2) used in the oligonucleotide conjugate selection.

Glycosyl donor 1 was prepared in seven steps from mannose according to literature methods. Then, the β-mannosylation conditions of Crich were modified by use of excess glycosyl acceptor (as compared to substoichiometric acceptor, as described by Crich). This modification suppressed overglycosylation of the acceptor (at nitrogen) and preserved a good diastereomeric ratio (13:1) at the β-mannose center. The nitrogen was protected as a carbamate to give 2. Sinay coupling with 3 then proceeded to give 4 in 70% isolated yield, after separation of a small amount (1:4) of the minor β-anomer. Global deprotection gave the $Man_4$ cyclohexylamine intermediate in nearly quantitative yield. This product was subjected to diazotransfer to give the azide 5. In this case, using 10 mol % $CuSO_4$ catalyst and six equivalents of $TfN_3$ gave better yields than Wong's method using 1 mol % catalyst and three equivalents of $TfN_3$.

Selection Process and Further Investigations

The ssDNA-dsDNA hybrid library formed according to FIG. 14 *a-d* was incubated with 2G12, and the 2G12-bound library fraction was captured with protein A beads. The 2G12-bound library fraction was eluted from the beads by thermal denaturation and subjected to PCR with biotinylated primer 2 to give the $2^{nd}$-generation library in purely dsDNA format (FIGS. 14*f* and 14*k*), which gave the expected sharp 80-bp band on the PAGE gel (lane 9). The library was converted back to its hairpin form in three steps: 1) removal of primer-2-derived biotinylated strand, 2) polymerase extension with an overhanging biotinylated strand to afforded 120-bp product (FIGS. 14*h* and 14*k*, lane 10), and 3) removal of the biotinylated strand from the 120-bp duplex and polymerase extension in the presence of dATP, dCTP, dGTP and EdUTP, afforded the $2^{nd}$-generation library in duplex hairpin form (FIG. 14*k*, lane 11, identical to lane 2).

The cycle of library generation and selection was repeated; enrichment was assessed by monitoring the number of PCR cycles required to regenerate the library. Rounds 2, 4, and 6 included a negative selection to remove aptamers that bound to protein A beads. No improvement was observed between rounds 5, 6 and 7, so the selection was terminated and the resulting PCR products were cloned. Twenty clones were randomly selected for sequencing. Seventeen sequences were obtained, which included two pairs of duplicates and fifteen unique sequences with no apparent similarity (FIG. 12). These oligonucleotides contained 7-14 Ts, reflecting the affinity of 2G12 for multiple carbohydrate moieties. These observations suggest that the selection may not have converged on the highest affinity aptamers. Future selections may be improved by limiting the number of positions containing EdU and increasing the stringency of the selection with the inclusion of a competitor.

Six clones were chosen for further evaluation (4/5, 16/23, 18, 19, 21, 22). The single-stranded portions of these clones were synthesized and glycosylated (see Supporting Information). Both PAGE and mass spectral analysis confirmed that the CuAAAC glycosylation step resulted in a significant portion of fully glycosylated product, though it was generally mixed with species lacking 1-2 glycosylations (see Example 17). All six of the glycosylated clones bound to 2G12 in a filter binding assay. Three clones containing 10 glycosylation sites were chosen for further analysis. Clones 4/5, 16/23 and 18 displayed moderate affinity for 2G12 with values of $K_d$=270±40 nM, 220±50 nM and 330±30 nM, respectively (FIG. 16*a*). Importantly, no binding was observed with the initial library or with a random oligonucleotide containing ten glycosylated residues. Therefore 2G12 binding is not simply the result of polyvalent interactions with multiple glycosylated residues.

The binding determinants of clone 16/23 were further dissected (FIG. 16*b*). The duplex form of clone 16/23 bound 2G12 significantly less efficiently than the single stranded version. No binding was observed in the absence of glycosylation. Gratifyingly, binding was significantly diminished in the presence of gp120, indicating that gp120 and clone 16/23 compete for the same site on 2G12.

A series of mutagenesis experiments on clone 16/23 were conducted, starting with truncation at both the 5' and 3' ends in short increments (FIG. 17, entries 1-8). The extreme ends are not essential for binding to 2G12; however, significant reduction in affinity was observed when the truncations extended beyond the first and last glycosylation sites. Point mutagenesis was performed, replacing each glycosylated EdU residue with cytosine (FIG. 17, entries 9-21). Seven of these mutations produced little change in the value of $K_d$; however, mutations in the $2^{nd}$, $4^{th}$, and $10^{th}$ glycosylation positions (entries 11, 13 and 19) caused a drastic loss of binding ($K_d$>>800 nM). Glycoaptamers containing only these three glycoslyation sites (entries 20 and 21) failed to bind to 2G12, indicating that glycoslyation of these sites is necessary but not sufficient for 2G12 binding. Glycosylation at the remaining sites may be important for the gross conformational features of the aptamer. Both of these findings are consistent with mutagenesis studies that showed only a small subset of gp120's dozen high-mannose glycans are required for 2G12 recognition. Significantly, these results are the first to demonstrate that the specific arrangement of carbohydrates—rather than high carbohydrate density or a large number of copies—is responsible for good mimicry of the epitope.

In certain embodiments, this work demonstrates the feasibility of using directed evolution to optimize the clustering of glycans for multivalent interaction with a target protein.

Exemplary Methods of the Invention

In certain embodiments, the invention relates to a method, comprising the steps of:
(a) combining an oligonucleotide, a first DNA polymerase, and a plurality of deoxyribonucleotide triphosphates,
wherein
the oligonucleotide comprises a first primer binding site on the 5' end, a randomized region, and a stem-loop region;
the randomized region is located between the first primer binding site and the stem-loop region;
the stem-loop region comprises a second primer binding site; and at least one of the deoxyribonucleotide triphosphates comprises a reactive substituent;
thereby forming an extended oligonucleotide comprising an original strand and an extended strand, wherein the extended strand comprises at least one reactive substituent;
(b) combining a plurality of modifying compounds and the extended oligonucleotide under reaction conditions, thereby forming a modified extended oligonucleotide comprising the original strand and a modified extended strand; and
(c) combining a primer complementary to the second primer binding site, a second DNA polymerase, the modified extended oligonucleotide, and a plurality of deoxyribonucleotide triphosphates
thereby creating a duplex with the original strand and displacing the modified extended strand.

In certain embodiments, the invention relates to a method, comprising the steps of:
(a) combining a plurality of oligonucleotides, a first DNA polymerase, and a plurality of deoxyribonucleotide triphosphates,
wherein
the oligonucleotides comprise a first primer binding site on the 5' end, a randomized region, and a stem-loop region;
the randomized region is located between the first primer binding site and the stem-loop region;
the stem-loop region comprises a second primer binding site; and
at least one of the deoxyribonucleotide triphosphates comprises a reactive substituent;
thereby forming a plurality of extended oligonucleotides comprising an original strand and an extended strand, wherein the extended strand comprises at least one reactive substituent;
(b) combining a plurality of modifying compounds and the plurality of extended oligonucleotides under reaction conditions,
thereby forming a plurality of modified extended oligonucleotides comprising the original strand and a modified extended strand; and
(c) combining a plurality of primers complementary to the second primer binding site, a second DNA polymerase, the plurality of modified extended oligonucleotides, and a plurality of deoxyribonucleotide triphosphates
thereby creating duplexes with the original strands and displacing the modified extended strands.

In certain embodiments, the invention relates to any one of the aforementioned methods, wherein oligonucleotide is in the form of a partial stem-loop.

In certain embodiments, the invention relates to any one of the aforementioned methods, wherein the randomized region consists of about 15-35, about 15, about 20, about 25, about 30, or about 35 nucleobases.

In certain embodiments, the invention relates to any one of the aforementioned methods, wherein the randomized region consists of about 25 nucleobases.

In certain embodiments, the invention relates to any one of the aforementioned methods, wherein the deoxyribonucleotide triphosphate comprising a reactive substituent is an unnatural deoxyribonucleotide triphosphate.

In certain embodiments, the invention relates to any one of the aforementioned methods, wherein the reactive substituent is ethynyl.

In certain embodiments, the invention relates to any one of the aforementioned methods, wherein the deoxyribonucleotide triphosphate comprising a reactive substituent is 5-ethynyl-deoxyuridine triphosphate.

In certain embodiments, the invention relates to any one of the aforementioned methods, wherein no thymidine triphosphate is used in step (a).

In certain embodiments, the invention relates to any one of the aforementioned methods, wherein the extended oligonucleotide has a hairpin configuration.

In certain embodiments, the invention relates to any one of the aforementioned methods, further comprising the step of purifying the extended oligonucleotide, thereby forming a purified extended oligonucleotide.

In certain embodiments, the invention relates to any one of the aforementioned methods, wherein the modifying compound comprises an azide.

In certain embodiments, the invention relates to any one of the aforementioned methods, wherein the modifying compound comprises an azide and a sugar moiety.

In certain embodiments, the invention relates to any one of the aforementioned methods, wherein the modifying compound is represented by the following formula:

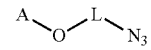

wherein
A represents a branched or unbranched oligosaccharide consisting of about 3 to about 15 saccharide moieties;
L represents a linker;
the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; or a heteroaryl diradical; any of which may be optionally substituted; and
R represents H or alkyl.

In certain embodiments, the invention relates to any one of the aforementioned methods, wherein the modifying compound is represented by formula III

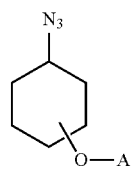

Formula III wherein A represents a branched or unbranched oligosaccharide consisting of about 3 to about 15 saccharide moieties.

In certain embodiments, the invention relates to any one of the aforementioned methods, wherein the modifying compound is:

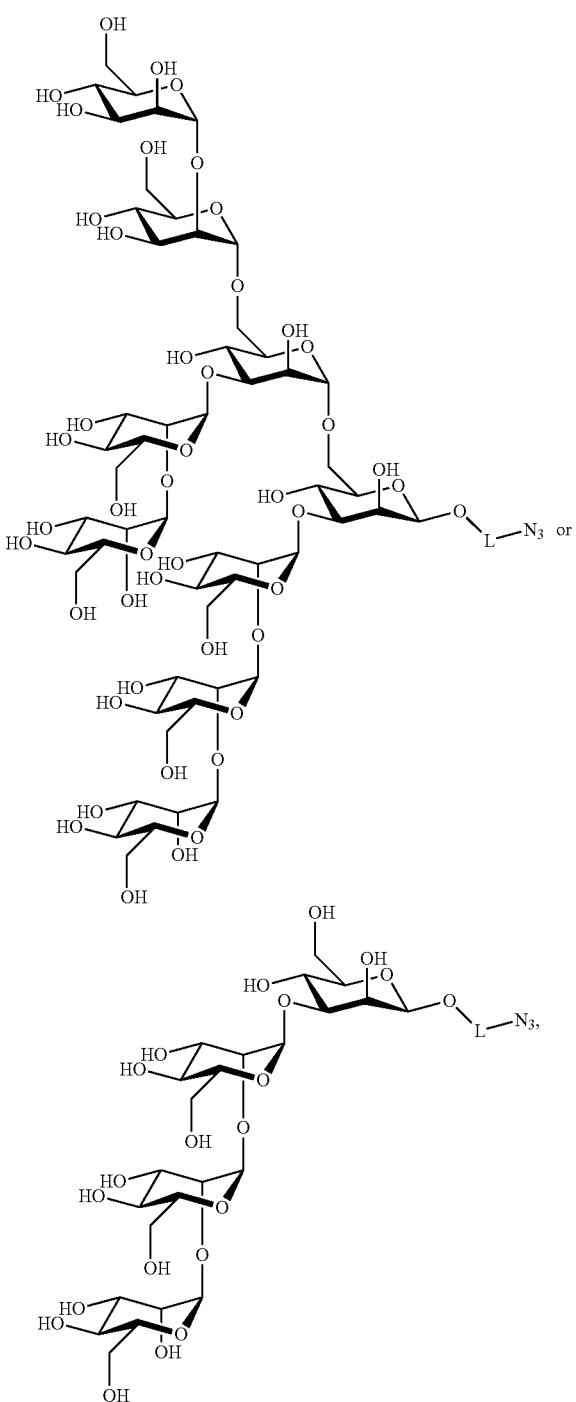

wherein

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to any one of the aforementioned methods, wherein the modifying compound is represented by formula I or formula II

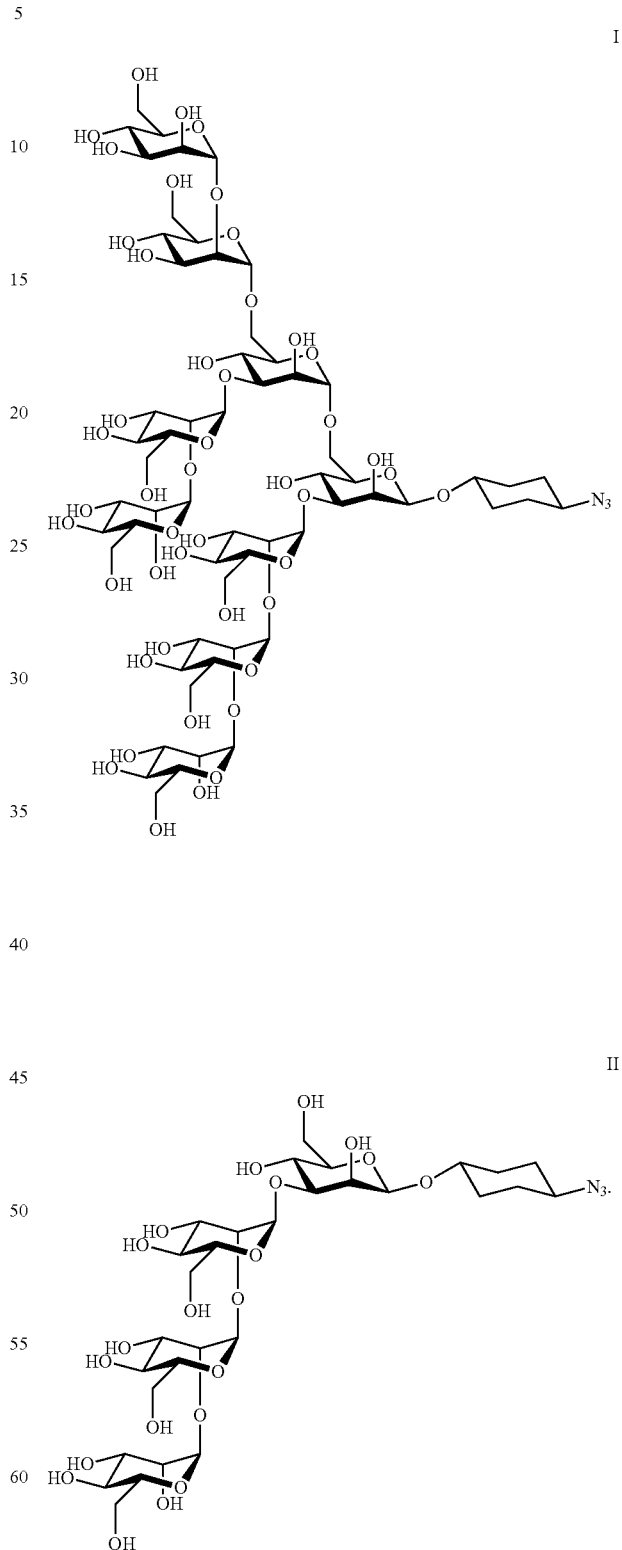

In certain embodiments, the invention relates to any one of the aforementioned methods, wherein the modifying compound is selected from the group consisting of 13
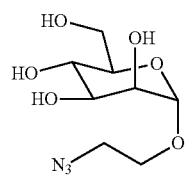
14
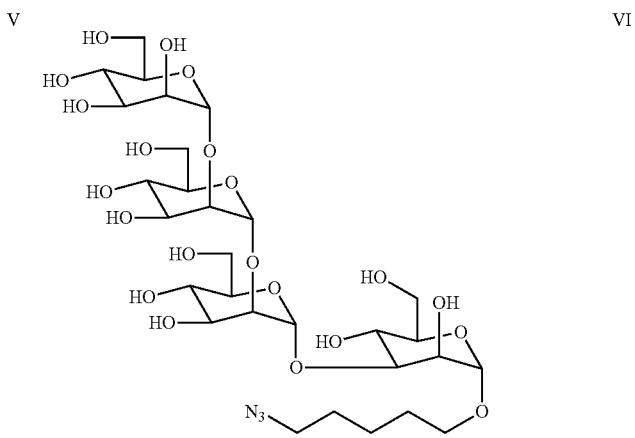
V
VI
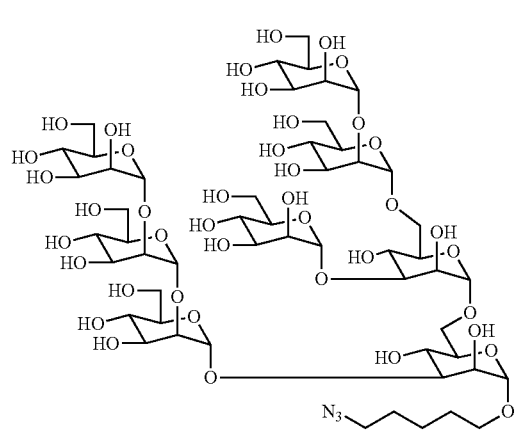
VII
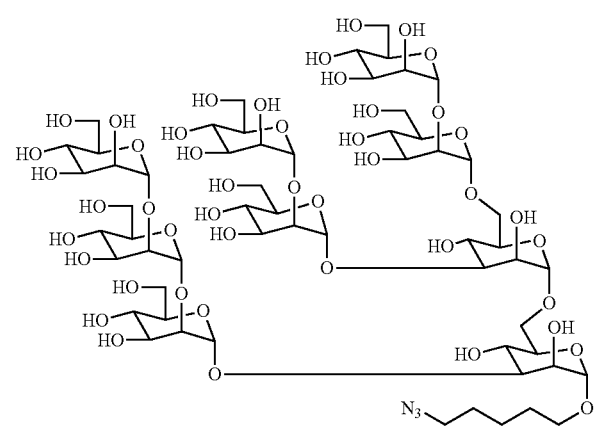
VIII
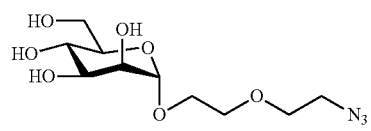
IX
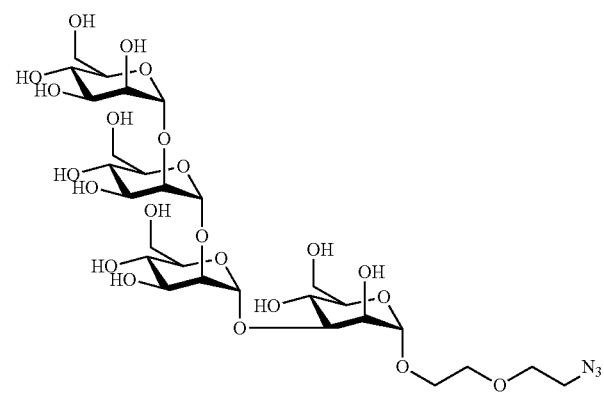
X -continued
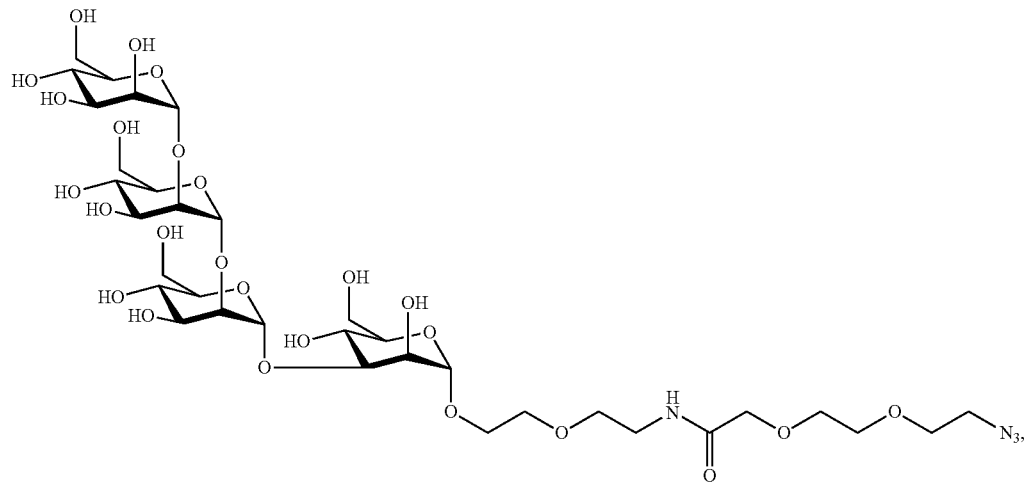
XI
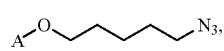
XII
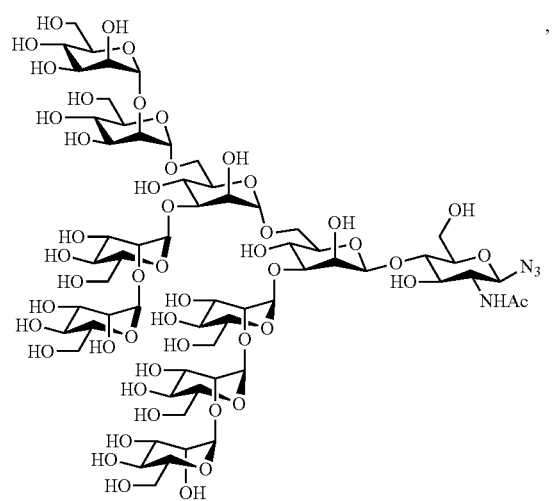
XIII
, and
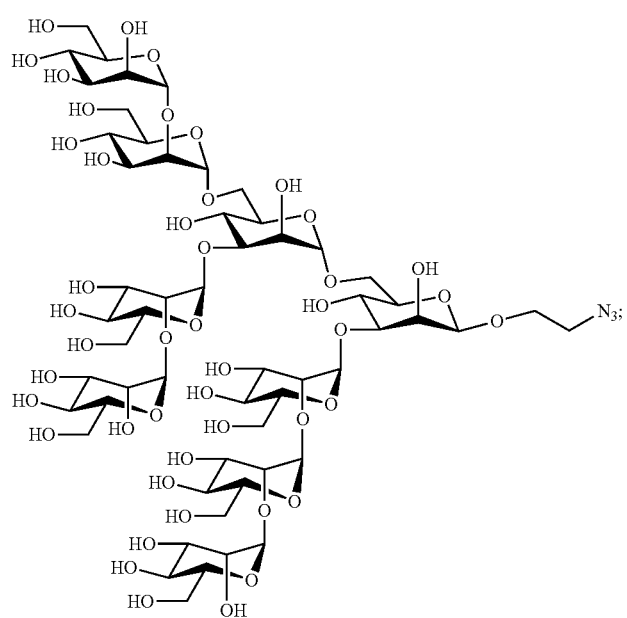
XIV wherein A represents a branched or unbranched oligosaccharide consisting of about 3 to about 15 saccharide moieties.

In certain embodiments, the invention relates to any one of the aforementioned methods, wherein the reaction conditions include copper catalysis or ruthenium catalysis.

In certain embodiments, the invention relates to any one of the aforementioned methods, wherein the reaction conditions include copper catalysis.

In certain embodiments, the invention relates to a method, comprising the steps of:
combining a plurality of modified single-stranded oligonucleotides and a target protein;
isolating the modified single-stranded oligonucleotides that bind to the target protein, thereby identifying a plurality of selected oligonucleotides;
amplifying the plurality of selected oligonucleotides, thereby forming a plurality of double-stranded oligonucleotides; and
preparing from the plurality of double-stranded oligonucleotides a plurality of regenerated selected oligonucleotides.

In certain embodiments, the invention relates to any one of the aforementioned methods, further comprising the step of exposing the plurality of regenerated selected oligonucleotides to the target protein.

In certain embodiments, the invention relates to any one of the aforementioned methods, wherein the target protein is an antibody.

In certain embodiments, the invention relates to any one of the aforementioned methods, wherein the target protein is a non-human antibody.

In certain embodiments, the invention relates to any one of the aforementioned methods, wherein the target protein is the 2G12 antibody.

In certain embodiments, the invention relates to any one of the aforementioned methods, wherein the modification comprises a sugar moiety attached to the oligonucleotide.

In certain embodiments, the invention relates to any one of the aforementioned methods, wherein the modification comprises a sugar moiety attached to the oligonucleotide via a triazole moiety.

In certain embodiments, the invention relates to a method, comprising the steps of:
(a) combining a plurality of oligonucleotides, a first DNA polymerase, and a plurality of deoxyribonucleotide triphosphates,
wherein
the oligonucleotides comprise a first primer binding site on the 5' end, a randomized region, and a stem-loop region;
the randomized region is located between the first primer binding site and the stem-loop region;
the stem-loop region comprises a second primer binding site; and
at least one of the deoxyribonucleotide triphosphates comprises a reactive substituent;
thereby forming a plurality of extended oligonucleotides comprising an original strand and an extended strand, wherein the extended strand comprises at least one reactive substituent;
(b) combining a plurality of modifying compounds and the plurality of extended oligonucleotides under reaction conditions,
thereby forming a plurality of modified extended oligonucleotides comprising the original strand and a modified extended strand;
(c) combining a plurality of primers complementary to the second primer binding site, a second DNA polymerase, the plurality of modified extended oligonucleotides, and a plurality of deoxyribonucleotide triphosphates
thereby creating duplexes with the original strands, displacing the modified extended strands, and forming a plurality of modified single-stranded oligonucleotides;
(d) combining the plurality of modified single-stranded oligonucleotides and a target protein;
(e) isolating the modified single-stranded oligonucleotides that bind to the target protein, thereby identifying a plurality of selected oligonucleotides;
(f) amplifying the plurality of selected oligonucleotides, thereby forming a plurality of complementary oligonucleotides; and
(g) preparing a plurality of regenerated selected oligonucleotides from the plurality of complementary oligonucleotides.

In certain embodiments, the invention relates to any one of the aforementioned methods, wherein the oligonucleotide has the form of a partial stem-loop.

In certain embodiments, the invention relates to any one of the aforementioned methods, wherein the randomized region consists of about 15-35, about 15, about 20, about 25, about 30, or about 35 nucleobases.

In certain embodiments, the invention relates to any one of the aforementioned methods, wherein the randomized region consists of about 25 nucleobases.

In certain embodiments, the invention relates to any one of the aforementioned methods, wherein the deoxyribonucleotide triphosphate comprising a reactive substituent is an unnatural deoxyribonucleotide triphosphate.

In certain embodiments, the invention relates to any one of the aforementioned methods, wherein the reactive substituent is ethynyl.

In certain embodiments, the invention relates to any one of the aforementioned methods, wherein the deoxyribonucleotide triphosphate comprising a reactive substituent is 5-ethynyl-deoxyuridine triphosphate.

In certain embodiments, the invention relates to any one of the aforementioned methods, wherein no thymidine triphosphate is used in step (a).

In certain embodiments, the invention relates to any one of the aforementioned methods, wherein the extended oligonucleotide has a hairpin configuration.

In certain embodiments, the invention relates to any one of the aforementioned methods, further comprising the step of purifying the extended oligonucleotide, thereby forming a purified extended oligonucleotide.

In certain embodiments, the invention relates to any one of the aforementioned methods, wherein the modifying compound comprises an azide.

In certain embodiments, the invention relates to any one of the aforementioned methods, wherein the modifying compound comprises an azide and a sugar moiety.

In certain embodiments, the invention relates to any one of the aforementioned methods, wherein the modifying compound is represented by the following formula:

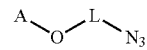

wherein
A represents a branched or unbranched oligosaccharide consisting of about 3 to about 15 saccharide moieties;

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to any one of the aforementioned methods, wherein the modifying compound is represented by formula III

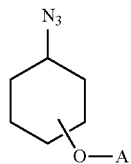

Formula III wherein A represents a branched or unbranched oligosaccharide consisting of about 3 to about 15 saccharide moieties.

In certain embodiments, the invention relates to any one of the aforementioned methods, wherein the modifying compound is represented by one of the following formulae:

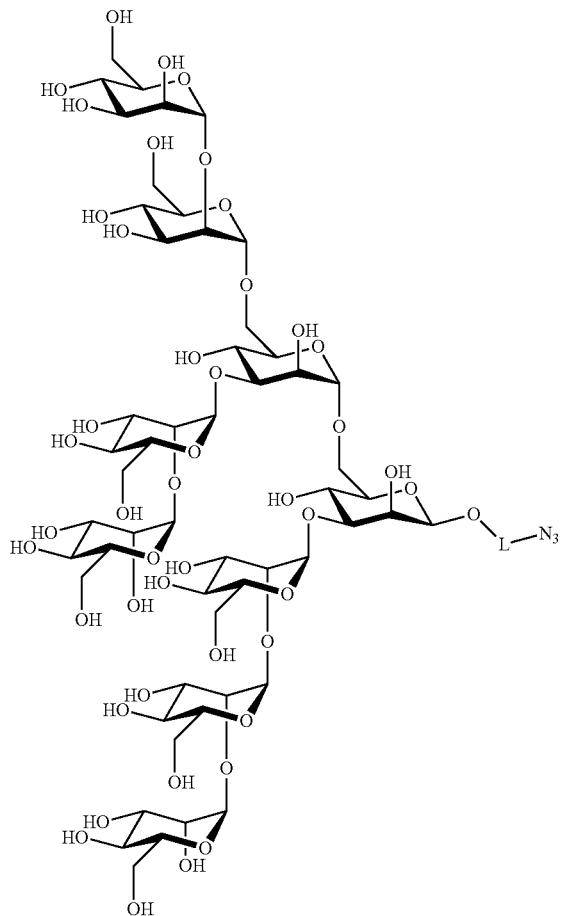

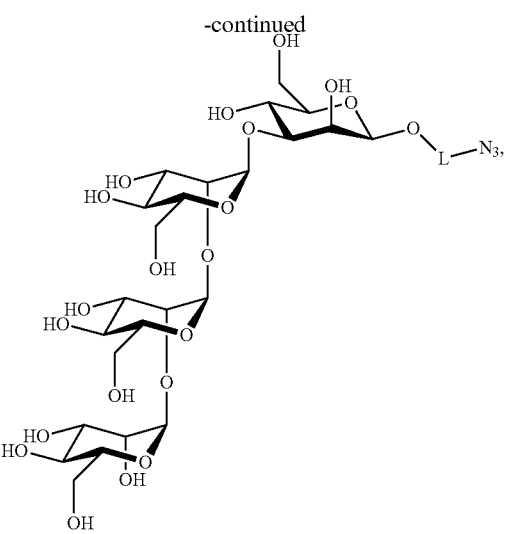

wherein

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to any one of the aforementioned methods, wherein the modifying compound is represented by formula I or formula II

I

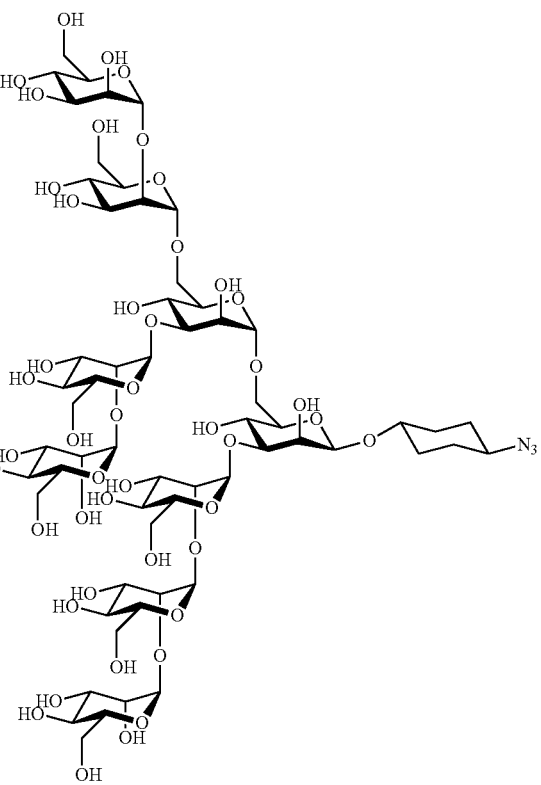

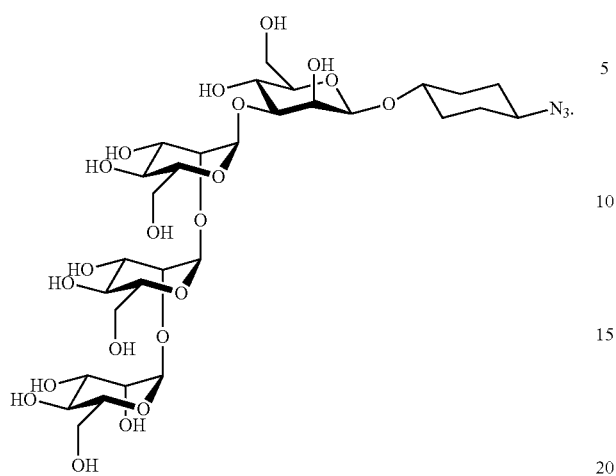
II
In certain embodiments, the invention relates to any one of the aforementioned methods, wherein the modifying compound is selected from the group consisting of
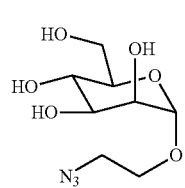
V
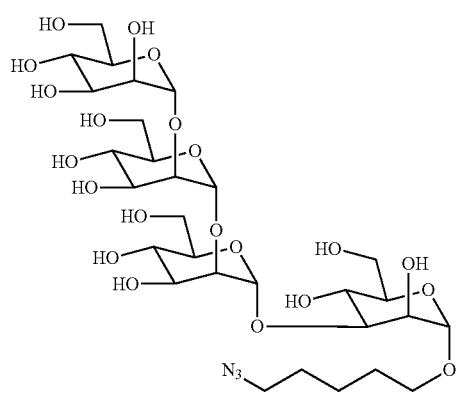
VI
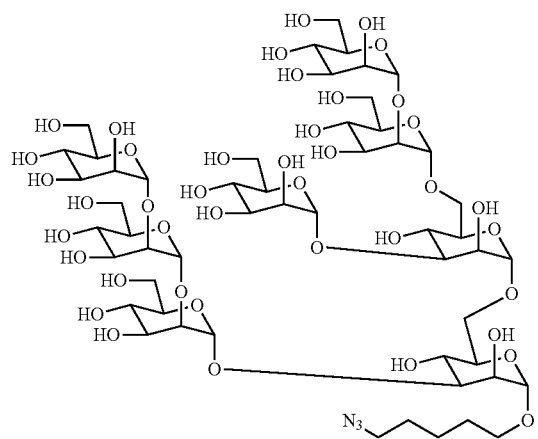
VII
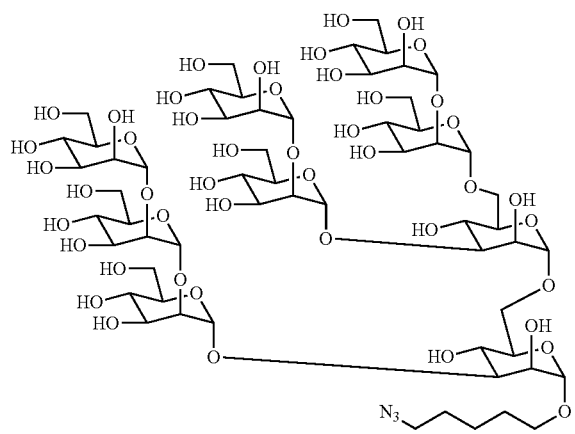
VIII -continued
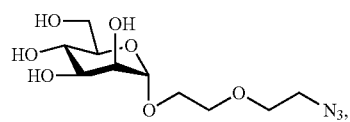
IX
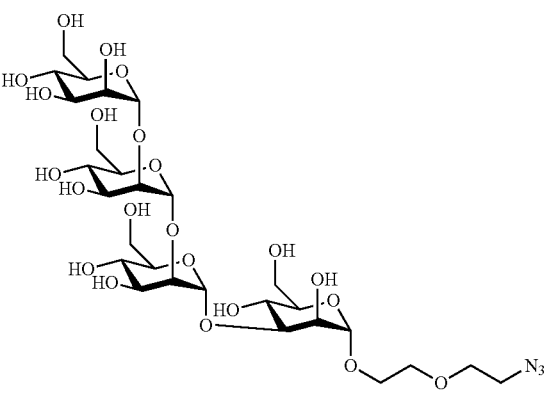
X
XI
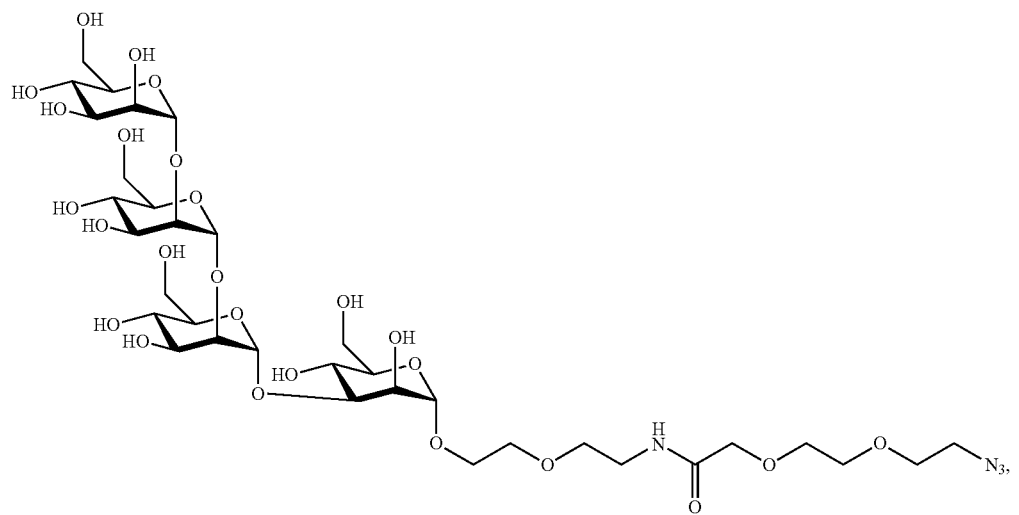
XII
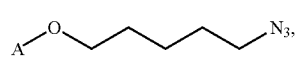

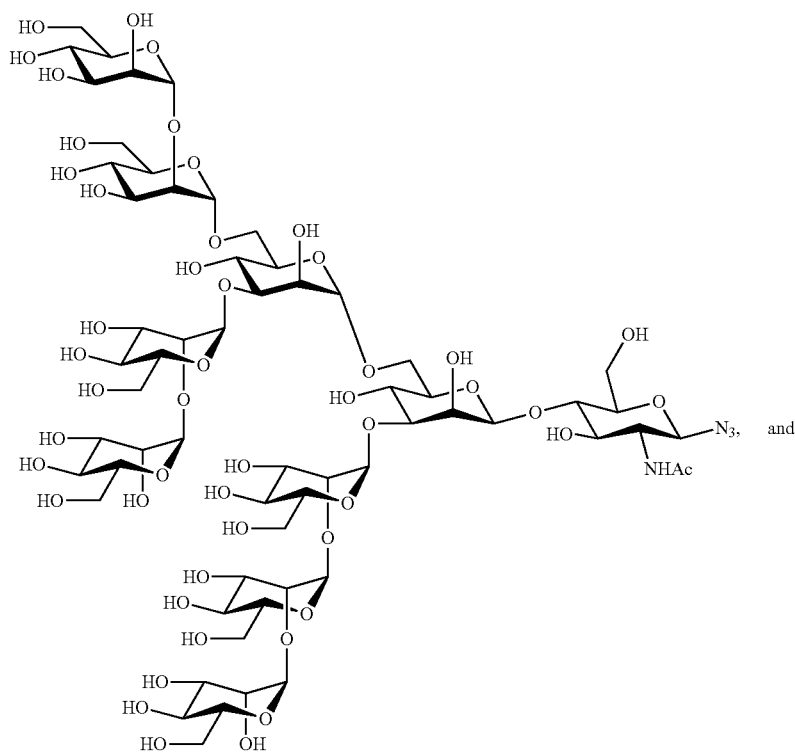
XIII
and
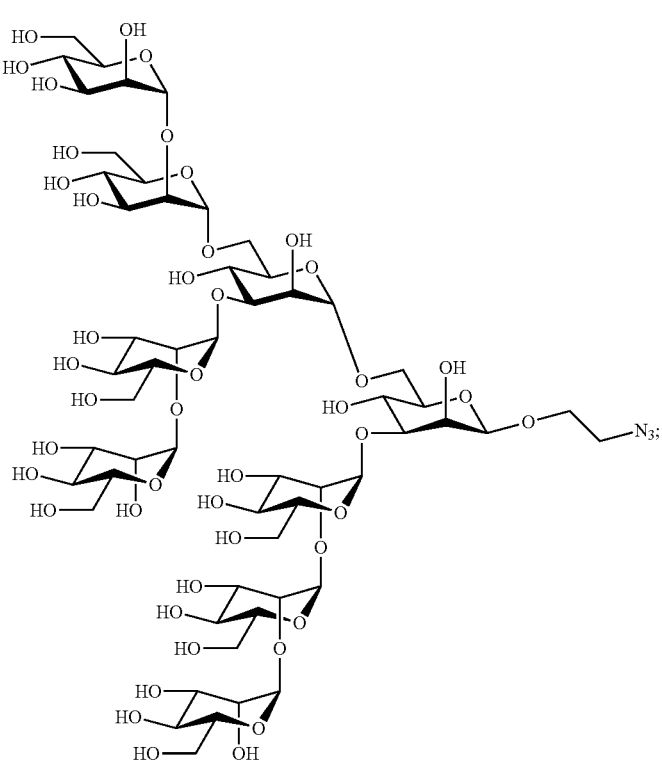
XIV wherein A represents a branched or unbranched oligosaccharide consisting of about 3 to about 15 saccharide moieties.

In certain embodiments, the invention relates to any one of the aforementioned methods, wherein the reaction conditions include copper catalysis or ruthenium catalysis.

In certain embodiments, the invention relates to any one of the aforementioned methods, wherein the reaction conditions include copper catalysis.

In certain embodiments, the invention relates to any one of the aforementioned methods, further comprising the step of exposing the plurality of regenerated selected oligonucleotides to the target protein.

In certain embodiments, the invention relates to any one of the aforementioned methods, wherein the target protein is an antibody.

In certain embodiments, the invention relates to any one of the aforementioned methods, wherein the target protein is a non-human antibody.

In certain embodiments, the invention relates to any one of the aforementioned methods, wherein the target protein is the 2G12 antibody.

Exemplary Compounds of the Invention

In certain embodiments, the invention relates to a compound comprising a sugar moiety and an azide.

In certain embodiments, the invention relates to a compound of the following formula:

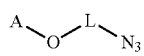

wherein

A represents a branched or unbranched oligosaccharide consisting of about 3 to about 15 saccharide moieties;

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to a compound of formula III

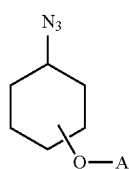

Formula III wherein A represents a branched or unbranched oligosaccharide consisting of about 3 to about 15 saccharide moieties.

In certain embodiments, the invention relates to any one of the aforementioned compounds, wherein the compound is represented by one of the following formulae:

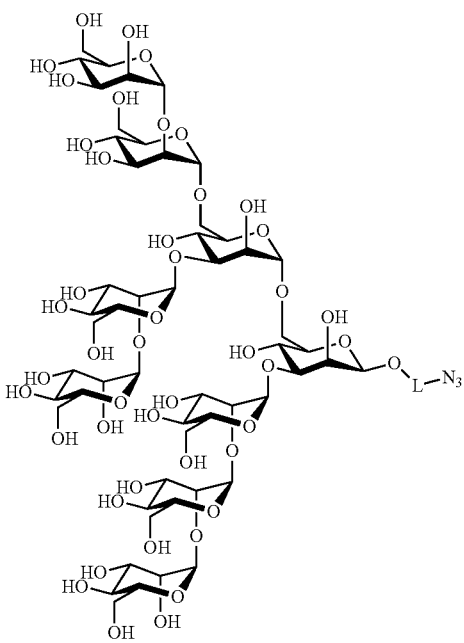

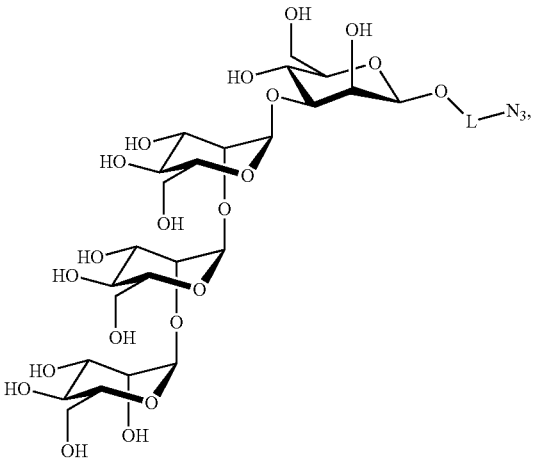

wherein

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to any one of the aforementioned compounds, wherein the compound is represented by formula I or formula II I
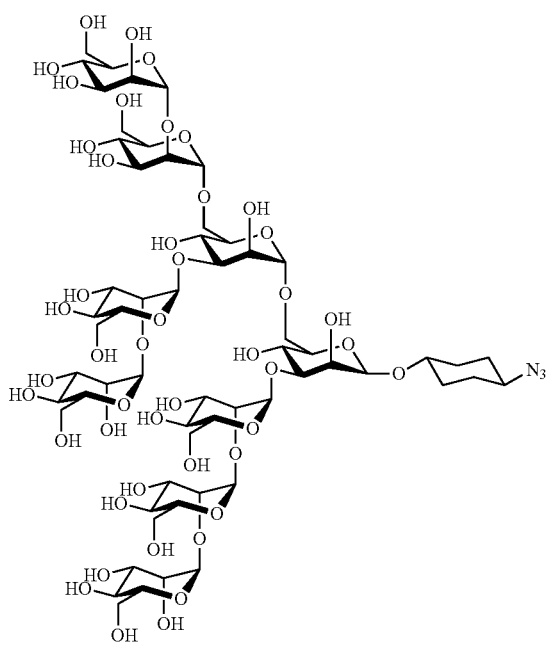
II
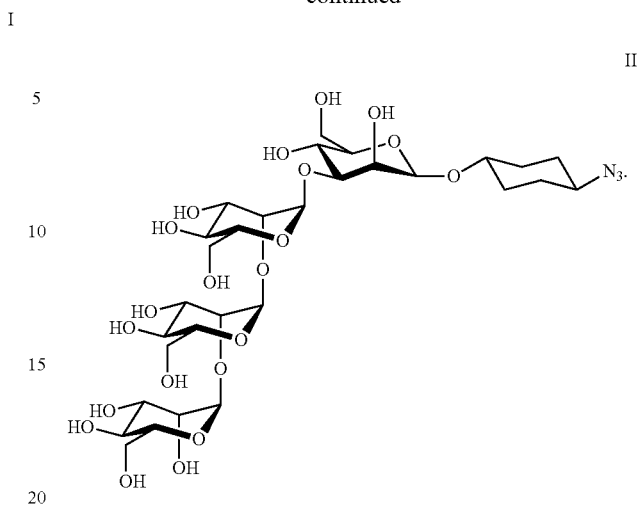
In certain embodiments, the invention relates to any one of the aforementioned compounds, wherein the compound is selected from the group consisting of
V
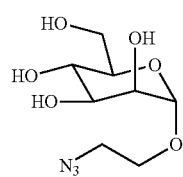
VI
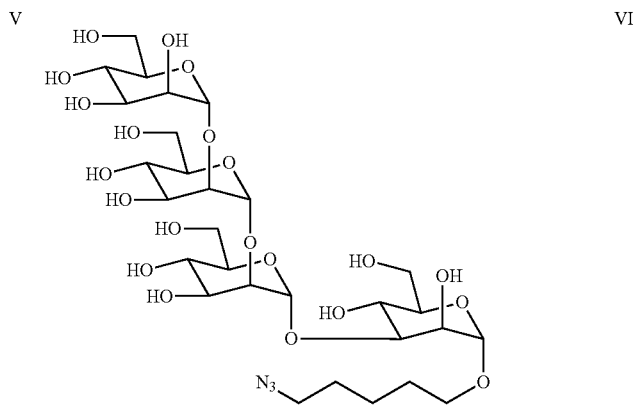
VII
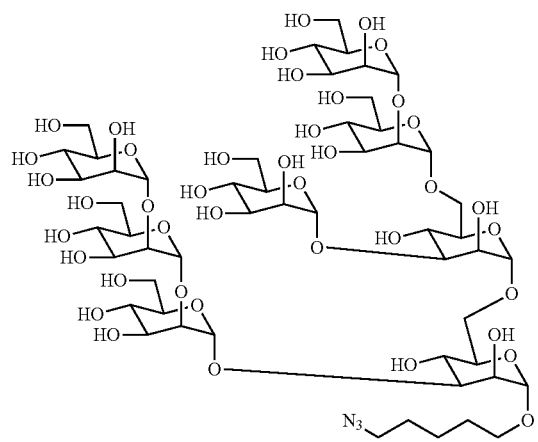
VIII
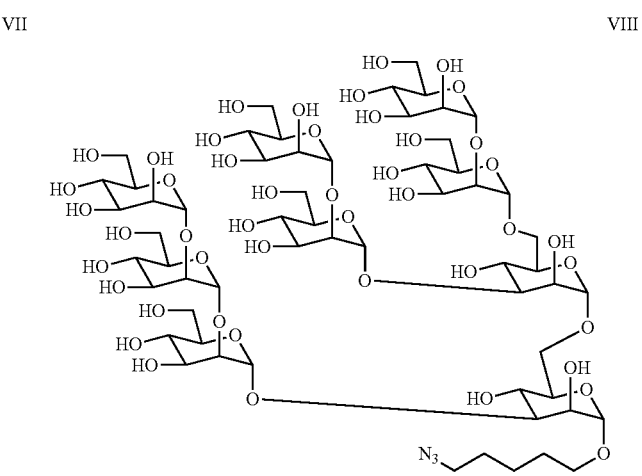

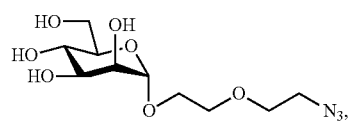
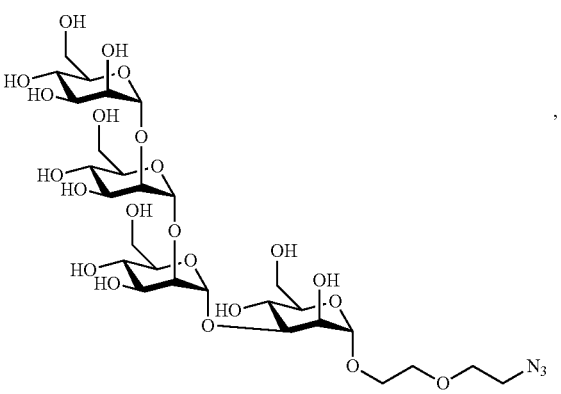
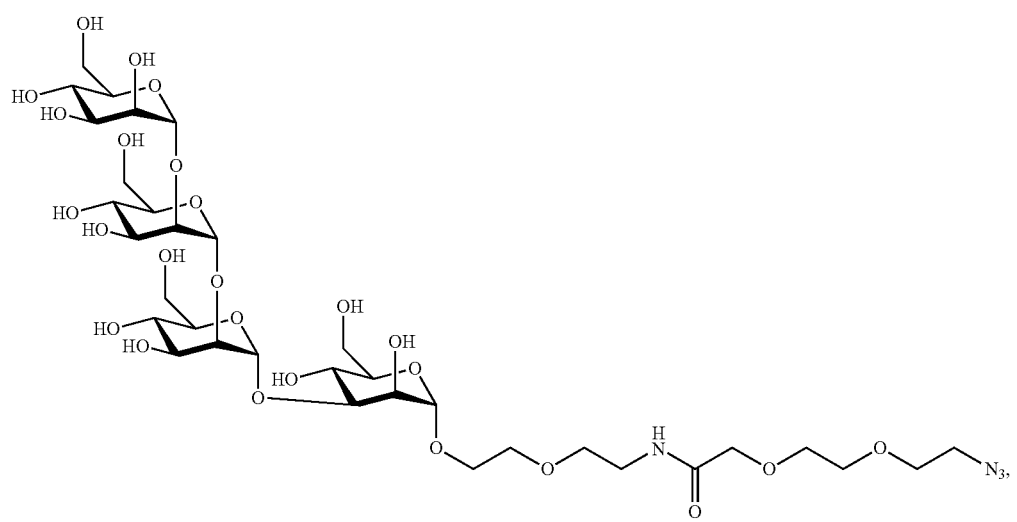
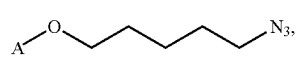

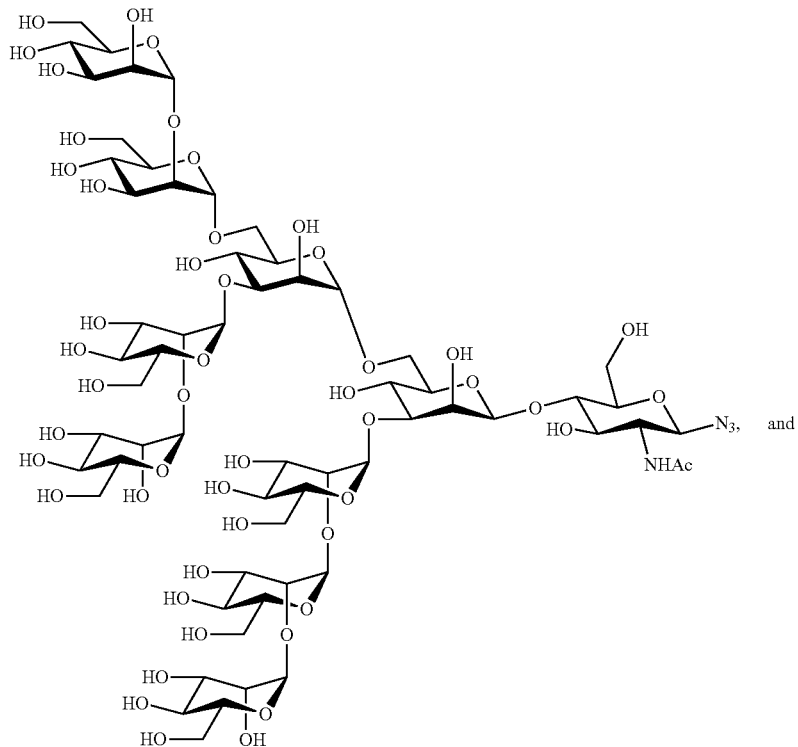

XIII

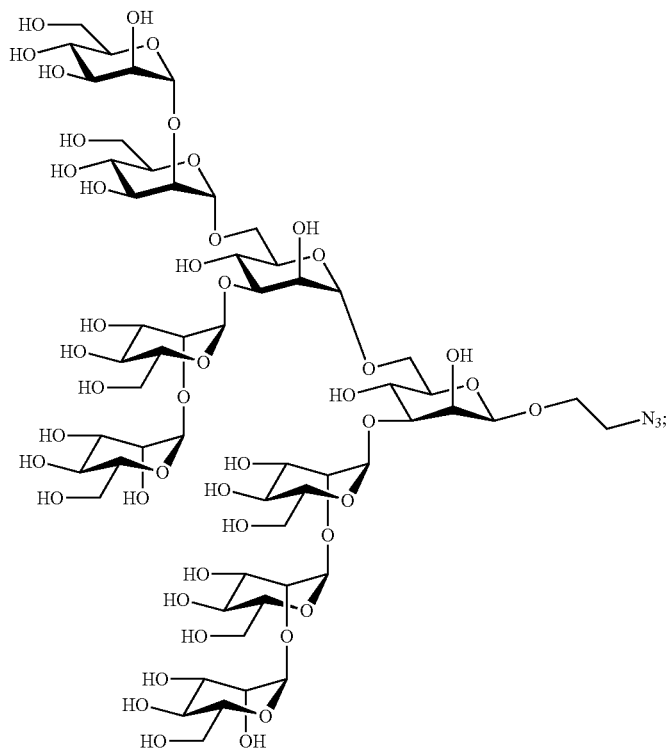

XIV wherein A represents a branched or unbranched oligosaccharide consisting of about 3 to about 15 saccharide moieties.

Exemplary Oligonucleotides of the Invention

In certain embodiments, the invention relates to an oligonucleotide, wherein the oligonucleotide comprises at least one non-natural deoxynucleoside; and the non-natural deoxynucleoside comprises an oligosaccharide moiety and a triazole moiety.

In certain embodiments, the invention relates to an oligonucleotide, wherein the oligonucleotide comprises at least one non-natural deoxynucleoside of the following formula:

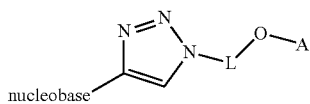

wherein

A represents a branched or unbranched oligosaccharide consisting of about 3 to about 15 saccharide moieties;

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to an oligonucleotide, wherein the oligonucleotide comprises at least one non-natural deoxynucleoside of the following formula

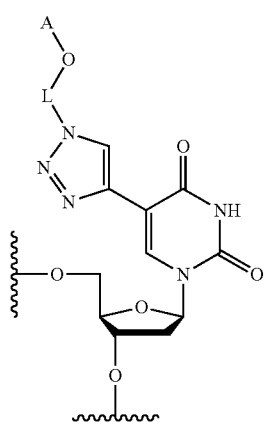

wherein

A represents a branched or unbranched oligosaccharide consisting of about 3 to about 15 saccharide moieties;

L represents a linker;

the linker is a linear or branched $C_2$-$C_{18}$-alkanediyl; a linear or branched $C_2$-$C_{30}$-alkanediyl optionally interrupted by one or more non-adjacent —O—, one or more —NR—, or one or more —C(=O)—; 1,3-cyclohexanediyl; 1,4-cyclohexanediyl; 4-methyl-1,3-cyclohexanediyl; an aryl diradical; a monosaccharide diradical; a disaccharide diradical; or a heteroaryl diradical; any of which may be optionally substituted; and R represents H or alkyl.

In certain embodiments, the invention relates to an oligonucleotide, wherein the oligonucleotide comprises at least one non-natural deoxynucleoside of formula IV

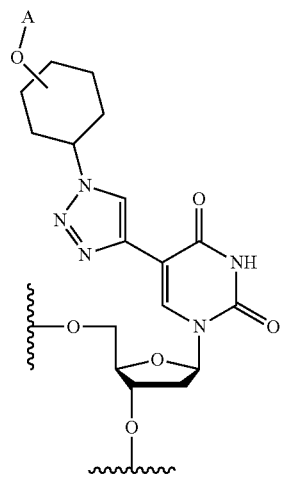

Formula IV wherein A represents a branched or unbranched oligosaccharide consisting of about 3 to about 15 saccharide moieties.

In certain embodiments, the invention relates to any one of the aforementioned oligonucleotides, consisting of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or 56 nucleobases.

Exemplary Formulations of the Invention

In certain embodiments, the invention relates to a formulation, comprising:

any one of the aforementioned compounds or oligonucleotides; and an immunogenic carrier.

In certain embodiments, the invention relates to a formulation, consisting essentially of:

any one of the aforementioned compounds or oligonucleotides; and an immunogenic carrier.

In certain embodiments, the invention relates to a formulation, consisting of:

any one of the aforementioned compounds or oligonucleotides; and an immunogenic carrier.

In certain embodiments, the immunogenic carrier helps elicit a response from the immune system of a mammal upon administration of the formulation to a mammal in need thereof.

In certain embodiments, the immunogenic carrier is coupled to any one of the aforementioned compositions.

In certain embodiments, the immunogenic carrier is Keyhold Limpet Hemocyanin (KLH). KLH is one of the most widely employed carrier proteins for this purpose. KLH is an effective carrier protein for several reasons. Its large size and numerous epitopes generate a substantial immune response, and the abundance of lysine residues for coupling haptens allows a high hapten:carrier protein ratio, increasing the likelihood of generating hapten-specific antibodies. In addition, because KLH is derived from the limpet, a gastropod, it is phylogenetically distant from mammalian proteins, thus reducing false positives in immunologically-based research techniques in mammalian model organisms.

In certain embodiments, the immunogenic carrier is the outer membrane protein complex (OMPC) of *Neisseria meningitidis*.

In certain embodiments, the formulation further comprises a T-helper epitope. In certain embodiments, the T-helper epitope is coupled to any one of the aforementioned compositions.

In certain embodiments, the invention relates to a formulation, comprising:

an adjuvant; and any one of the aforementioned compounds or oligonucleotides.

In certain embodiments, the invention relates to a formulation, consisting essentially of:

an adjuvant; and any one of the aforementioned compounds or oligonucleotides.

In certain embodiments, the invention relates to a formulation, consisting of:

an adjuvant; and any one of the aforementioned compounds or oligonucleotides.

In certain embodiments, the adjuvant is any substance that acts to accelerate, prolong, or enhance antigen-specific immune responses when used in combination with any one of the aforementioned compositions.

In certain embodiments, the adjuvant comprises an aluminum salt. In certain embodiments, the adjuvant comprises aluminum hydroxide or aluminum phosphate.

In certain embodiments, the adjuvant comprises a phosphate.

In certain embodiments, the adjuvant comprises squalene.

EXEMPLIFICATION

The invention now being generally described, it will be more readily understood by reference to the following examples which are included merely for purposes of illustration of certain aspects and embodiments of the present invention, and are not intended to limit the invention.

Example 1

Oligosaccharide Synthesis

Materials and Methods

Reagents were purchased from Sigma-Aldrich, Acros Organics, Fluka, Alfa Aesar, or Strem, and used without further purification unless otherwise noted. Toluene, THF, and DCM were dried by passage through activated alumina columns and stored under argon gas. Acetonitrile was distilled over calcium hydride. Glassware was flame-dried or dried in a 150° C. oven. Silicycle Siliaflash® P60 silica was used for column chromatography. All $^1$H and $^{13}$C NMR spectra were obtained on a Varian iNova 400 instrument in CDCl$_3$ and internally referenced to TMS; or D$_2$O, internally or externally referenced to sodium 3-(trimethylsilyl)propanesulfonate. Chemical shifts are reported in parts per million (ppm), and coupling constants are reported in Hz. LC/MS analysis was performed on a Waters Acquity UPLC chromatograph with a reverse phase C$_{18}$ or C$_8$ column, and a Waters Micromass Z/Q mass detector. Optical rotation was measured using a Jasco digital polarimeter Infrared spectra were obtained using a Varian 640-IR spectrometer with a ZnSe ATR.

Experimental Procedures

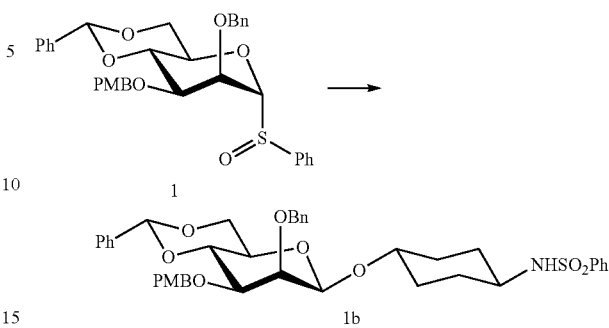

To a 50 mL flask was added 717 mg (1.22 mmol) of starting material 1. This was cooled to −78° C. and azeotroped with toluene twice. Then, 8 mL of dry dichloromethane, along with 606 mg (2.44 mmol) of tri tert-butylpyrimidine and freshly flame-dried powdered 4-Å molecular sieves were added. This was cooled to −78° C. and allowed to stir for 30 minutes. After this time, 0.16 mL (0.978 mmol) of distilled triflic anhydride was added slowly. This was allowed to react for 30 minutes, then 630 mg (2.44 mmol) of acceptor in 8.5 mL of dichloromethane was added dropwise. After 1 hour, the reaction was allowed to slowly warm to −20° C., and quenched with saturated aqueous NaHCO$_3$ solution, then filtered through Celite. The solution was washed with 50 mL of saturated aqueous NaHCO$_3$ solution, then the aqueous phase was extracted with 3×50 mL ethyl acetate. The combined organic layers were dried with MgSO$_4$, filtered and concentrated. Crude mass was 2.00 g. Purified by flash column chromatography with 1:2:1----˃1:1.5:1 ethyl acetate/hexanes/dichloromethane. Final mass was 638 mg (0.891 mmol, 91%) based on Tf$_2$O) of 1b as a white foam. $^1$H NMR (400 MHz, CDCl$_3$): δ 7.89 (d, 2H, J=7.3 Hz), 7.60-7.17 (m, 15H), 6.82 (d, 2H, J=8.6 Hz), 5.59 (s, 1H), 4.93 (d, 1H, J=12.2 Hz), 4.83 (d, 1H, J=12.2 Hz), 4.55 (m, 4H), 4.26 (dd, 1H, J=4.9, 10.4 Hz), 4.17 (app t, 1H), 3.90 (app t, 1H), 3.79 (s, 3H), 3,79 (m, 1H), 3.59 (m, 1H), 3.53 (dd, 1H, J=9.8 Hz, 3.1 Hz), 3.27 (m, 1H), 3.18 (m, 1H), 1.97 (m, 1H), 1.85 (m, 3H), 1.40 (m, 1H), 1.24 (m, 3H). $^{13}$C-NMR (100 MHz, CDCl3, selected signals): δ 29.5, 31.0, 51.7, 55.4, 67.7, 68.7, 72.1, 74.7, 75.6, 76.1, 77.7, 78.6, 100.2, 101.5, 113.8, 126.2, 127.0, 127.7, 128.2, 128.3, 128.8, 129.0, 129.3, 130.4, 132.8, 137.7, 138.5, 141.1, 159.2. IR (cm$^{-1}$): 3267 (br), 2936, 2863, 1610 (s), 1512, 1448, 1325, 1246, 1159, 1076. HRMS (ESI+): calcd. for C$_{40}$H$_{46}$NO$_9$S$^+$ [M+H$^+$] 716.2893, found 716.2892.

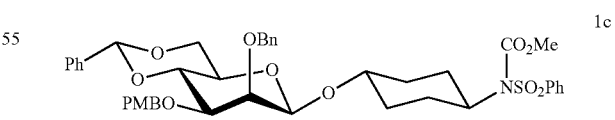

To a 25-mL round bottom flask was added 213 mg (5.32 mmol) of 60% wt NaH powder, and this was cooled to 0° C. A solution of 760 mg (1.06 mmol) of 1b in 8.5 mL of THF was added slowly. This was allowed to stir for 30 minutes, then 0.269 mL (3.19 mmol) of methyl chloroformate was added, along with 130 mg (1.06 mmol) of recrystallized DMAP. The cooling bath was removed, and the reaction progressed for 17 hours. After this time, the flask was cooled to 0° C. and quenched with saturated aqueous NH₄Cl solution. The organic phase was washed with 40 mL of NH₄Cl solution, then the aqueous phase was extracted with 3×40 mL of DCM. The combined organic layers were dried with MgSO₄, filtered and concentrated. Crude mass was about 1 g. Purification by flash column chromatograph in 1:2 ethyl acetate/hexanes gave a final mass of 724 mg (0.936 mmol, 88%) of 1c as a white foam. ¹H NMR (400 MHz, CDCl₃): δ 7.92 (d, 2H, J=8.6 Hz), 7.62 (app t, 1H), 7.57-7.44 (m, 6H), 7.40-7.27 (m, 6H), 7.20 (d, 2H, J=8.5 Hz), 6.83 (d, 2H, J=8.6 Hz), 5.61 (s, 1H), 4.98 (d, 1H, J=12.8 Hz), 4.88 (d, 1H, J=12.2 Hz), 4.61 (d, 1H, J=12.2 Hz), 4.55 (s, 1H), 4.53 (d, 1H, J=~12 Hz), 4.44 (m, 1H), 4.31 (dd, 1H, J=10.4 Hz, 4.9 Hz), 4.20 (app t, 1H), 3.94 (app t, 1H), 3.83 (d, 1H, J=2.7 Hz), 3.80 (s, 3H), 3.66 (s, 3H), 3.66 (m, 1H), 3.56 (dd, 1H, J=9.8 Hz, 2.4 Hz), 3.31 (m, 1H), 2.27 (m, 3H), 2.05 (m, 1H), 1.87 (m, 2H), 1.58 (m, 1H), 1.41 (m, 1H). ¹³C-NMR (100 MHz, CDCl3, selected signals): δ 28.6, 31.7, 33.3, 53.6, 55.4, 58.6, 67.7, 68.7, 72.1, 74.7, 76.1, 76.3, 77.7, 78.7, 100.3, 101.5, 113.8, 126.2, 127.6, 128.0, 128.2, 128.3, 128.9, 129.3, 130.5, 133.5, 137.7, 138.5, 140.3, 152.7, 159.2. IR (cm⁻¹): 2939, 2866, 1731, 1512, 1449, 1356, 1269, 1247, 1169, 1085, 1045, 733, 697. HRMS (ESI+): calcd. for $C_{42}H_{48}NO_{11}S^+$ [M+H⁺] 774.2948, found 774.2961.

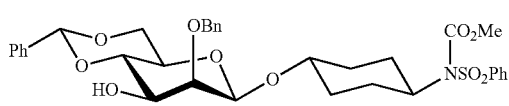

2

To a flask containing 2.04 g (2.64 mmol) of 1c was added 28 mL of DCM and 1.55 mL of 1 M pH 7 phosphate buffer. This was cooled to 0° C., and 1.44 g (6.34 mmol) of DDQ was added. This was allowed to stir for 1 hour, then quenched with aqueous NaHCO₃ solution. This was diluted with DCM, and the organic phase was washed with 375 mL of water. The aqueous phase was extracted with 3×300 mL DCM, then the combined organic layers were dried with MgSO₄, filtered, and concentrated. Purification by flash chromatography (1:2 ethyl acetate/hexanes) afforded 1.53 g (2.34 mmol, 87%) of 2 as an off-white foam. ¹H NMR (400 MHz, CDCl₃): δ 7.90 (d, 2H, J=7.3 Hz), 7.60 (app t, 1H) 7.57-7.27 (m, 12H), 5.52 (s, 1H), 5.05 (d, 1H, J=11.6 Hz), 4.67 (s, 1H), 4.65 (d, 1H, J=12.2), 4.43 (m, 1H), 4.29 (dd, 1H, J=10.4 Hz, 4.9 Hz), 3.92-3.63 (m, 5H), 3.64 (s, 3H), 3.31 (m, 1H), 2.36-2.11 (m, 5H), 1.86 (m, 2H), 1.61-1.40 (m, 2H). ¹³C-NMR (100 MHz, CDCl3, selected signals): δ 28.5, 31.7, 33.4, 53.6, 58.5, 67.2, 68.7, 70.9, 75.8, 76.4, 78.9, 79.4, 100.3, 102.1, 126.4, 120.0, 128.1, 128.4, 128.5, 128.6, 128.9, 129.2, 133.5, 137.3, 138.2, 140.3, 152.6. IR (cm⁻¹): 3528 (br), 2949, 2872, 1733, 1449, 1358, 1272, 1171, 1090, 751, 700. HRMS (ESI+): calcd. for $C_{34}H_{40}NO_{10}S^+$ [M+H⁺] 654.2373, found 654.2366.

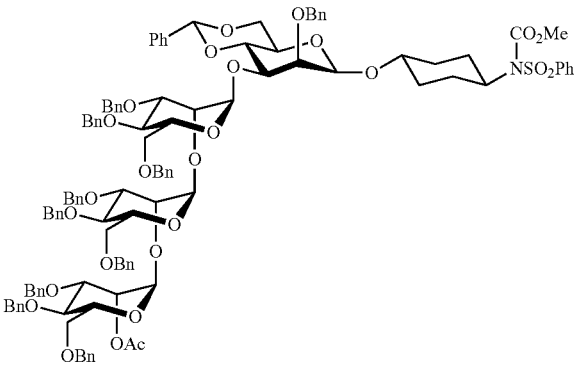

4

210 mg (0.333 mmol) of 2 and 700 mg of 3 (0.500 mmol) in a 25 mL flask were dissolved in toluene and cooled to −78° C. Vacuum was applied and the cooling bath was removed and allowed to warm to room temperature as the toluene evaporated. This procedure was repeated twice. The residue was redissolved in 12 mL of acetonitrile, and freshly flame-dried 4-Å molecular sieves were added, and this was allowed to stir for 1 hour. The flask was then wrapped in foil, cooled to 0° C., and 525 mg (0.799 mmol) Sinaÿ reagent (p-BrC₆H₄)₃N⁺SbCl₆⁻, was added. This was allowed to react at 0° C. for 30 minutes, then at room temperature for 30 minutes. After this time, 1 mL triethylamine was added, and the reaction was filtered through Celite and concentrated in vacuo. The crude residue was purified by flash chromatography with 1:3.5:1 ethyl acetate/hexanes/DCM to give 440 mg (0.230 mmol, 69%) 4 as a white foam. ¹H NMR (400 MHz, CDCl₃): δ 7.92 (d, 2H, J=6.4 Hz), 7.62 (t, 1H), 7.53 (app t, 2H), 7.43 (d, 2H, J=7.3 Hz), 7.39 (d, 2H, J=7.0 Hz), 7.37-6.96 (m, 50H+residual CHCl₃), 6.93 (app t, 1H), 5.53 (s, 1H), 5.40 (s, 1H), 5.34 (s, 1H), 5.24 (s, 1H), 4.98 (s, 1H), 4.9-3.6 (complex region), 3.66 (s, 3H), 3.60-3.40 (m, 4H), 3.33 (br d, 1H, J=11.0), 3.13 (m, 1H), 2.24 (m, 2H), 2.12, (s, 3H), 1.84 (m, 3H), 1.51 (m, 1H), 1.26 (m, 1H+grease). ¹³C-NMR (100 MHz, CDCl₃, selected signals): δ 28.5, 33.2, 53.5, 58.5, 67.3, 94.4, 99.6, 99.9, 100.0, 101.2, 126.0, 133.5, 133.5, 137.3, 138.2, 138.5. IR (cm⁻¹): 3029, 2863, 1735, 1452, 1360, 1085, 1055, 736, 697. HRMS (ESI+): calcd. for $C_{117}H_{126}NO_{26}S^+$[M+H⁺] 1992.8289, found 1992.8224.

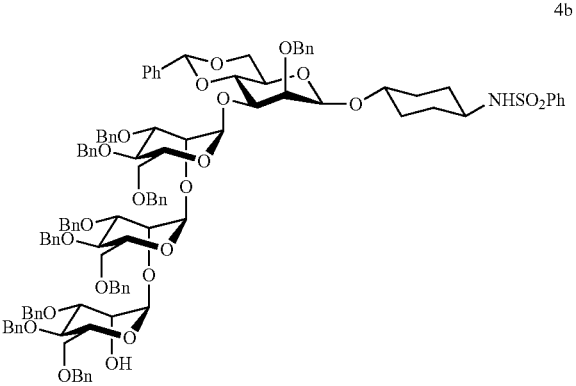

4b 100 mg (0.050 mmol) 4 was dissolved in 12 mL anhydrous methanol and 0.500 mL (2.00 mmol) of 25% wt NaOMe solution in methanol was added. After 3 hours, Amberlite IR-120 H+ ion exchange resin was added until the solution was neutral (NOTE: avoid acidifying beyond pH 4). The mixture was filtered through Celite® and concentrated to give 97 mg crude material. Purification by flash chromatography in 40% ethyl acetate/hexanes gave 87.6 mg (0.0463 mmol, 93%) product 4b as a white foam. $^1$H NMR (400 MHz, CDCl$_3$): δ 7.89 (d, 2H, J=8 Hz), 7.60 (app t, 1H), 7.55 (m, 2H), 7.43 (d, 2H, J=7.9 Hz) 7.40-7.07 (m, 52H+ residual CHCl$_3$), 6.92 (app t, 1H) 5.41 (s, 1H), 5.33 (s, 1H), 5.26 (s, 1H), 5.05 (s, 1H), 4.82-3.20 (complex region), 3.13 (m, 2H), 2.34 (s, 1H), 1.91 (m, 1H), 1.82 (m, 2H), 1.67 (m, 1H), 1.40 (m, 1H), 1.2-1.1 (m, 3H). $^{13}$C-NMR (100 MHz, CDCl3, selected signals): δ 31.1, 51.7, 67.4, 68.6, 69.2, 71.4, 72.2, 72.4, 73.3, 80.3, 99.9, 101.3, 126.0, 127.0, 127.2, 127.5, 127.7, 127.8, 127.9, 128.0, 128.1, 128.2, 128.3, 128.4, 128.5, 128.6, 129.3, 132.8, 138.2, 138.6. IR (cm$^{-1}$): 3460 (br) 3261 (br) 3063, 3027, 2920, 2862, 1453, 1362, 1073, 1055, 737, 697. HRMS (ESI+): calcd. for $C_{113}H_{121}NO_{23}S^+$ [M+H$^+$] 1892.8128, found 1892.8042.

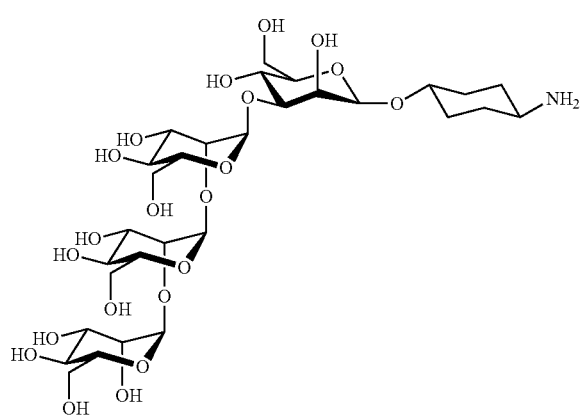

4c

Along with a stream of N$_2$, ammonia gas was condensed against a –78° C. cold finger into a –78° C.-cooled 500 mL 3-necked flask until ~200 mL had accumulated. 320 mg (13.8 mmol) Na$^0$ was then added, and the resulting blue solution was monitored for 1 hour to ensure that color did not disappear. 131 mg (0.0691 mmol) 4b in 3 mL THF was then added, and this was allowed to react at –78° C. for 2 hours. 1.11 g (20.7 mmol) of solid NH$_4$Cl was added portionwise, the cooling bath was removed, and the ammonia was blown off under a stream of nitrogen. The crude product was dissolved in minimal water and desalted by passage through a Biogel P-2 size exclusion gel column to give 51.8 mg (0.0678 mmol, 98%) compound 4c as a brittle colorless glass. $^1$H NMR (400 MHz, D$_2$O): δ 5.35 (s, 1H), 5.30 (s, 1H), 5.04 (s, 1H), 4.81 (s, 1H), 4.15-3.60 (m, 24H), 3.39 (m, 1H), 3.19 (m, 1H), 2.20-2.03 (m, 4H), 1.5-1.3 (m, 4H). $^{13}$C-NMR (100 MHz, CDCl3, selected signals): δ 30.9, 31.0, 31.9, 33.2, 52.0, 63.8, 69.0, 69.7, 69.8, 72.8, 73.2, 73.6, 76.1, 76.2, 78.8, 81.4, 83.5, 100.7, 103.5, 105.1. IR (cm$^{-1}$): 3300 (v br), 2925, 1739, 1629, 1448, 1363, 1030. HRMS (ESI+): calcd. for $C_{30}H_{54}NO_{21}^+$ [M+H$^+$] 764.3188, found 764.3184.

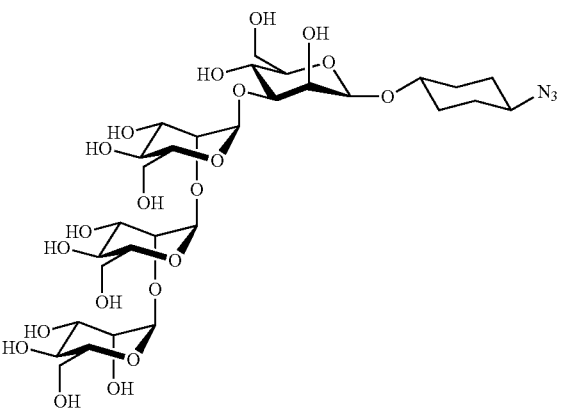

5

15.2 mg (0.234 mmol) sodium azide was suspended in a vial in 50 μL each of DCM and water. This was cooled to 0° C., and 20 μL (0.117 mmol) of triflic anhydride was added. After 2 hours, this was quenched with aqueous NaHCO$_3$ solution, and the aqueous layer was extracted twice with DCM. The combined organic layers containing triflyl azide were reduced to ~0.1 mL under vacuum.

Into a 5 mL flask containing 9 mg (0.0117 mmol) of 4c was added 125 μL water and 57 μL of 0.02 M aqueous CuSO$_4$ solution (0.0011 mmol). The triflyl azide solution (prepared above) was then added, followed by 0.5 mL of methanol. After 2.5 hours, the reaction was quenched with 10 mg (10 eq) solid NaHCO$_3$ and concentrated in vacuo. The crude material was desalted on a Biogel P-2 size exclusion gel column, and then purified by HPLC (gradient shown in FIG. 23). Product was detected by UV at 220 nm and eluted at ~18 minutes. Concentration of fractions afforded 6.6 mg (0.00842 mmol, 72%) of Man$_4$-azide (5), a colorless glass. $^1$H NMR (400 MHz, D$_2$O): δ 5.36 (s, 1H), 5.31 (s, 1H), 5.05 (s, 1H), 4.80 (s, 1H), 4.10-3.62 (m, 25H), 3.53-3.47 (m, 1H), 3.42-3.38 (m, 1H), 3.34 (s residual MeOH), 2.1-1.95 (m, 4H), 1.5-1.3 (m, 4H). $^{13}$C-NMR (100 MHz, D$_2$O, selected signals): δ 31.1, 31.2, 31.5, 32.9, 61.7, 63.8, 63.9, 69.0, 69.7, 69.8, 72.8, 73.2, 73.7, 76.1, 76.2, 78.9, 79.0, 81.4, 81.6, 83.5, 100.6, 103.5, 105.1. IR (cm$^{-1}$): 3344, 2933, 2096, 1629, 1367, 1124, 1055. HRMS (ESI+): calcd. for $C_{40}H_{52}N_3O_{21}^+$ [M+H$^+$] 790.3093, found 790.3087.

Example 2

General Biological Materials

The original oligonucleotide library, PCR primers and the library regeneration primer were purchased from Integrated DNA Technologies. A complete list of primers is in FIG. 1. Vent polymerase, Vent(exo) polymerase, Bst polymerase, T4 polynucleotide kinase, Exonuclease I, Taq polymerase and streptavidin magnetic beads were purchased from New England Biolabs. Centrisep desalting columns were purchased from Princeton Separations. Sephadex G-50 superfine resin was purchased from GE Healthcare. Antibody 2G12 was purchased from Immune Technology Corp. Protein A Dynabeads and a TOPO-TA cloning kit were purchased from Invitrogen. ATP (γ-$^{32}$P) was purchased from Perkin Elmer. Synthetic oligos were purchased from Integrated DNA Technologies of ELLA Biotech.

Example 3

Incorporation of Alkyne-Containing Thymidine Analogues

The original oligonucleotide library consists of a stem-loop region connected to a typical aptamer library—a randomized portion flanked by primer regions for aptamerfor and aptamerrev (FIG. 1). In a PCR tube, 40 pmol of library, 2.5 μL 10× Thermopol buffer (New England Biolabs), and 17 μL autoclaved $H_2O$ were combined, after which the temperature was raised to 95° C. for 15 seconds and allowed to cool to room temperature. Then, a 0.5 μL of a solution containing 10 mM deoxyadenosine triphosphate, 10 mM deoxycytosine triphosphate, 10 mM deoxyguanosine triphosphate, and 10 mM alkyne-containing thymidine triphosphate analogue 5-ethynyl-deoxyuridine (EdU) triphosphate (synthesis in Example 19) was added to afford a final concentration of 200 μM each. 8 U of Bst polymerase (large fragment) was added to the reaction, yielding a final reaction volume of 25 μL. The reaction was mixed and incubated at 60° C. for 2 minutes.

Example 4

Click Reaction

The reaction was diluted to 50 μL with $H_2O$ and transferred to a cap-less 0.5 mL microcentrifuge tube. 5 μL of 10 mM tris(3-hydroxypropyl-4-triazolylmethyl)amine (THPTA), 2 μL of 25 mM $CuSO_4$, and 5 μL of 35 mM mannose sugar-azide was added and the solution was mixed by pipetting. Then, 2 μL of freshly dissolved 250 mM sodium ascorbate was added followed by immediate mixing by pipetting. The microcentrifuge tube was quickly placed in a 5 mL round bottom flask and a rubber septum used to seal the tube, and argon was flushed into the flask for 5 minutes. The reaction was allowed to proceed for 2 hours. The modified DNA was then desalted twice through Centrisep desalting columns containing Sephadex G-50 superfine resin.

Note: Following the addition of sodium ascorbate, it is important to flush with argon as quickly as possible to minimize damage to the DNA.

Example 5

Strand Displacement

To the desalted reaction product, Thermopol buffer (1× final concentration), Aptamerfor primer (50 pmol), dNTPs (200 μM each final concentration), 8 U of Bst polymerase (large fragment) and $H_2O$ were added to a final volume of 50 μL. The reaction was incubated at 65° C. for 5 minutes followed immediately by buffer exchanging through a Centrisep column loaded with Sephadex G-50/binding buffer (20 mM Tris pH 7.5, 100 mM NaCl, 2 mM $MgSO_4$). Then, binding buffer plus 0.02% Tween-20 was added to a final volume of 50 μL and the solution was heated to 75° C. for 3 minutes and allowed to cool to room temperature.

Note: It is important to keep the mixture on ice prior to incubation at 65° C. to avoid unwanted side reactions. After strand displacement, it is important to quickly buffer exchange the reaction to remove dNTPs thus minimizing unwanted side reactions. At each desalting/buffer exchange step, the overall volume decreases. This is exacerbated by the inclusion of detergent (Triton X-100) in the polymerase buffer.

Figure 14:
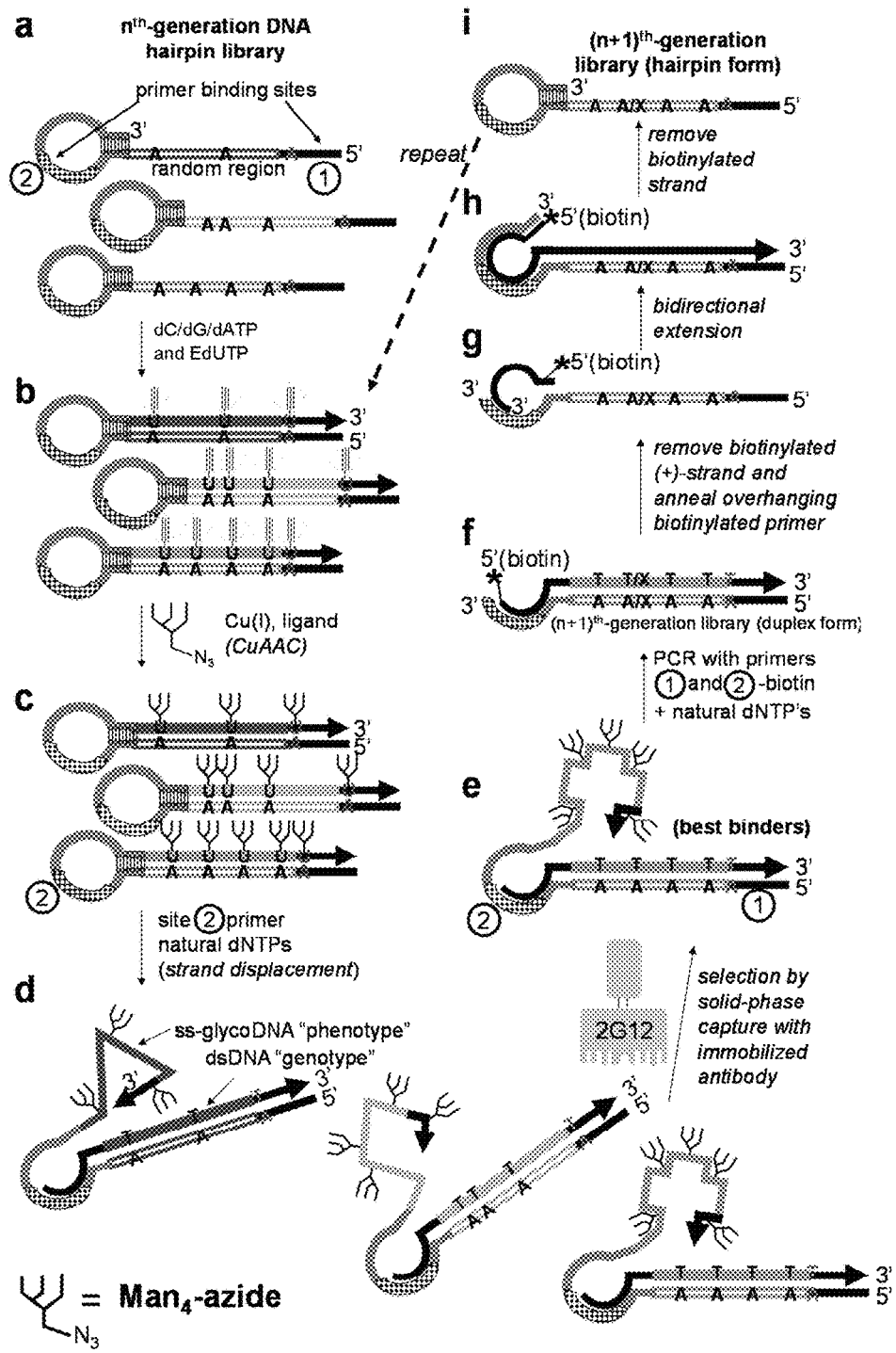
FIG. 14 (also referred to as "Scheme 1") depicts SELMA (SELection with Modified Aptamers). The starting point (a) is a synthetic library of ssDNA hairpins containing a stem-loop, an antisense random region (colored hollow bar) and primer sites 1 and 2. Polymerase extension with dNTP's (but alkyne-substituted EdUTP instead of dTTP) creates a dsDNA hairpin library (b) with alkynyl bases incorporated only in the (+)-sense strand. The alkynes are then glycosylated with carbohydrate-azide by CuAAAC chemistry, producing a glycosylated dsDNA library (c) Annealing of primer 1 inside the loop and polymerase extension with all-natural dNTPs results in displacement of the glycosylated strand, creating a library of glyco-ssDNA-dsDNA hybrids (d). The ss-glyco-DNA (+)-sense strand is now the "phenotype", whereas the tethered dsDNA copy contains no modifications and can undergo efficient PCR, serving as the "genotype". Thus, the functional structure and its genetic barcode are covalently attached, much as in mRNA display.[19] After selection by solid-phase capture with immobilized 2G12, the best binders (e) are amplified by PCR (or error-prone PCR) using natural dNTPs and primers 1 and 2 affording the $(n+1)^{th}$-generation library without the hairpin portion (f). The $(n+1)^{th}$-generation library is then restored to hairpin form (i) by bidirectional polymerase extension with an overhanging biotinylated primer and removal of the biotinylated strand (g-i).
Figure 15:
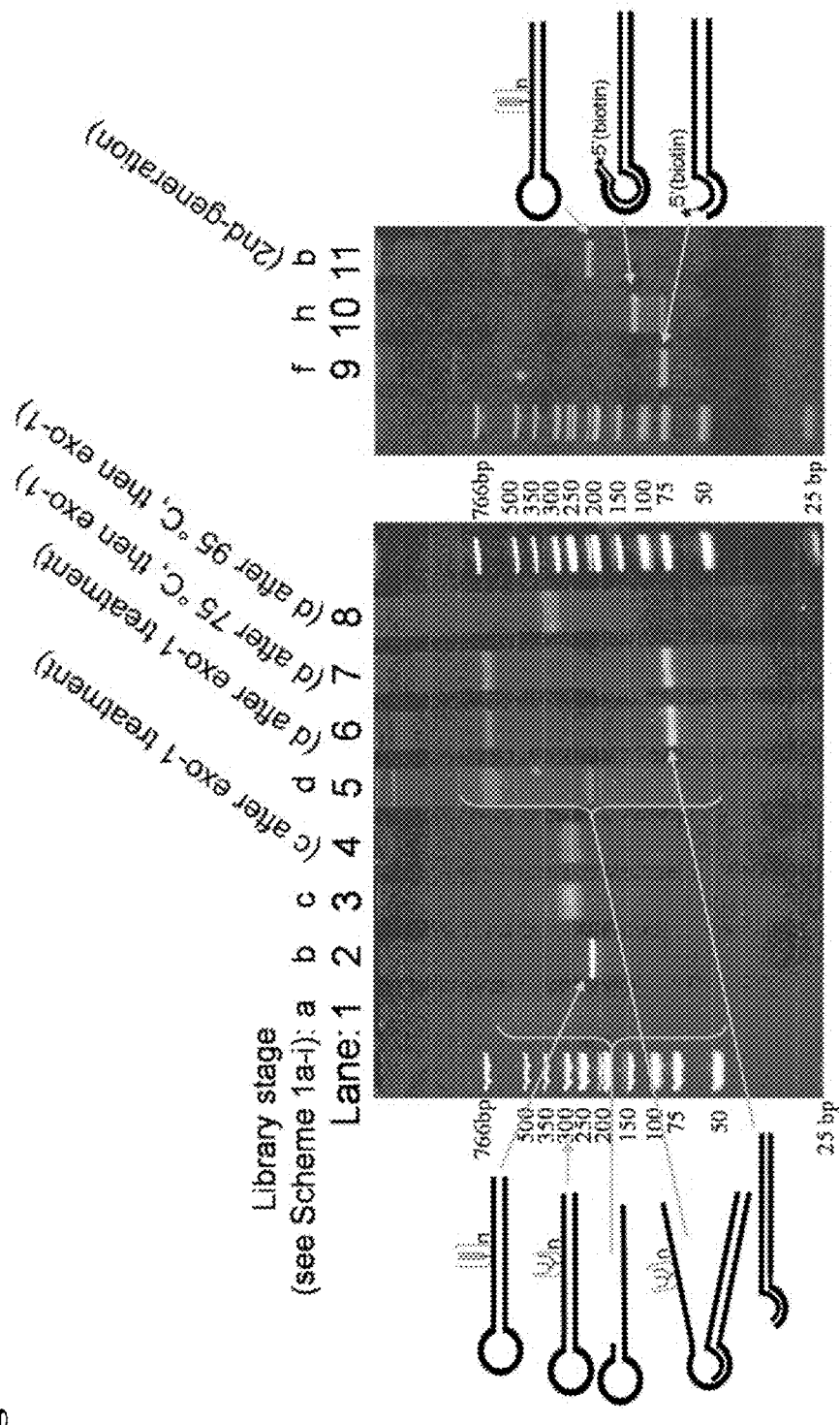
FIG. 15 depicts a PAGE analysis of the individual steps in a SELMA cycle.
Figure 18:
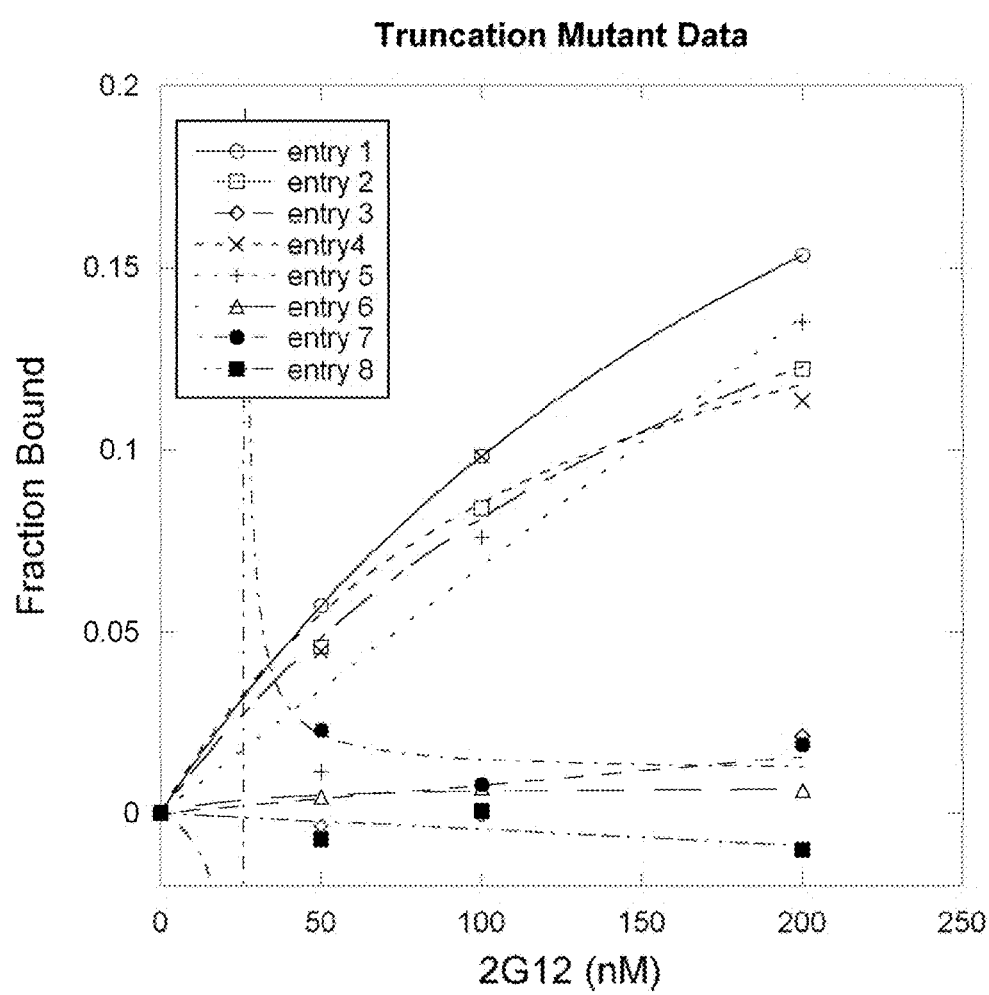
FIG. 18 depicts binding curves for truncation mutants of clone 16/23; entry numbers correspond to sequence numbers in FIG. 17.
Figure 19:
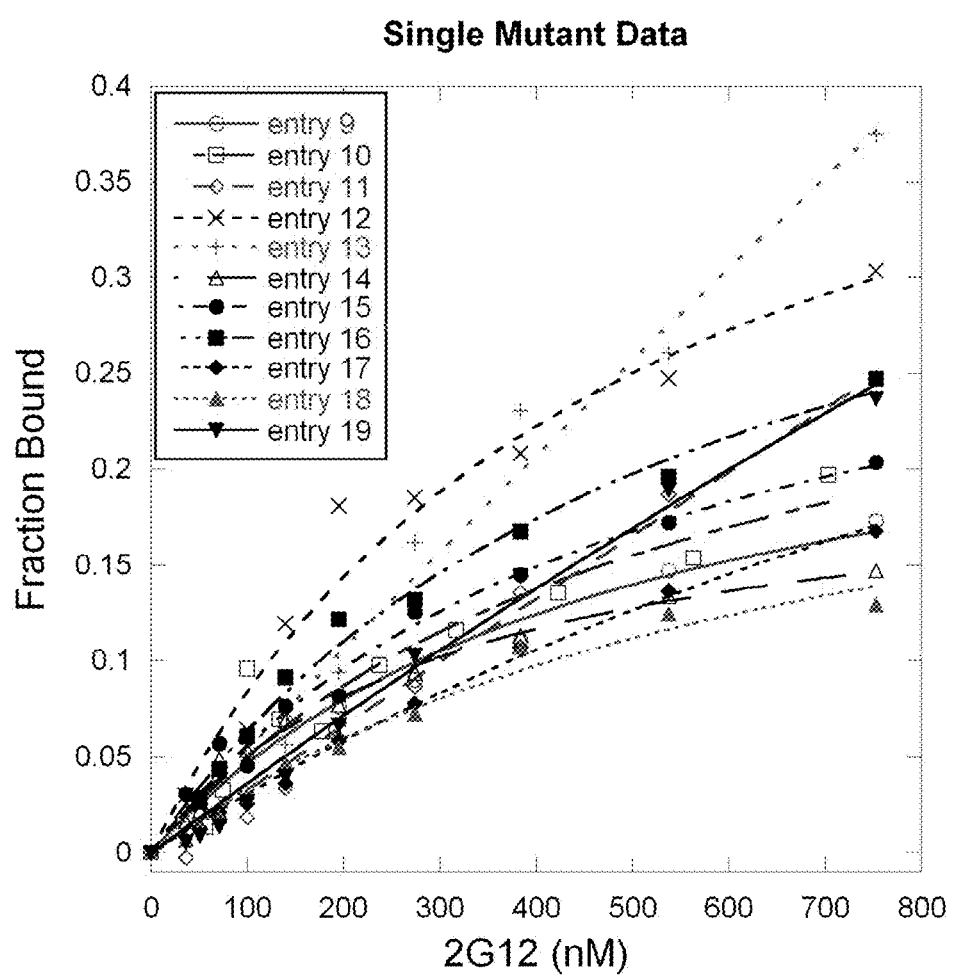
FIG. 19 depicts binding curves for single mutants of clone 16/23; entry numbers correspond to sequence numbers in FIG. 17.
Figure 20:
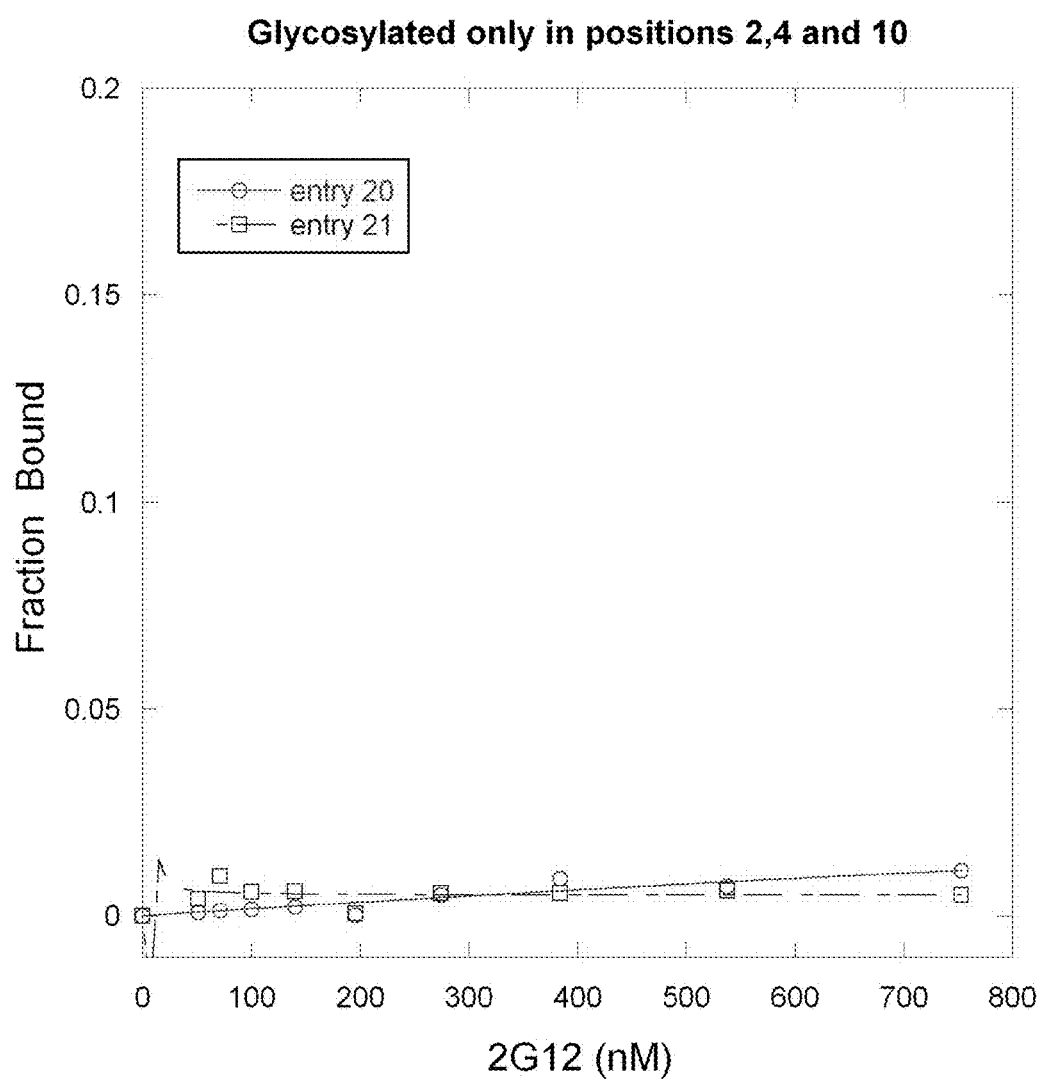
FIG. 20 depicts binding curves for mutants of clone 16/23 glycosylated only in positions 2, 4, and 10; entry numbers correspond to sequence numbers in FIG. 17.

The state of the library at each stage of a SELMA cycle was monitored by acrylamide gel analysis (FIG. 15). After polymerase extension in the presence of dATP, dCTP, dGTP and EdUTP, the alkyne-containing library had a duplex hairpin structure and ran (lane 2 and FIG. 14b) as a narrow, strongly-staining band with much less mobility than simple dsDNAs of similar length. Treatment of the library with $Man_4$-azide under CuAAAC conditions resulted in a more diffuse band with a still higher apparent molecular weight (lane 3 and FIG. 14c). Primer 2 (see FIG. 14a) was then added, together with natural dNTP's and polymerase extension resulted in the strand-displaced library (lane 5 and FIG. 14d). Several observations and control experiments were consistent with the assumed ssDNA-dsDNA hybrid structure of the library at this stage. First, it ran as a smear in the gel and importantly, treatment with exonuclease I (which digests the 3'-terminal ssDNA portion) resulted in the appearance of a sharp 80-bp band corresponding to the dsDNA portion (lane 6). By contrast, the glycosylated double stranded hairpins showed no change upon exonuclease treatment (lanes 3 vs. 4). Heating the hybrid to 95° C. (but not 75° C.) destabilized the duplex portion of the hybrid structure, allowing the glycosylated strand to reinvade, expel the unglycosylated single strand and return to the duplex hairpin structure, which is impervious to the exonuclease (compare lanes 4, 7 and 8).

Example 6

Selection for 2G12 Antibody Affinity

2G12 antibody was added to a final concentration of 50 nM and the solution was incubated at room temperature for 1 hr. Then, the mixture was added to 1.5 mg protein A Dynabeads and incubated for 45 minutes with rotation. The mixture was applied to a magnetic separator and the supernatant was removed by pipetting. Then, the mixture was washed with 100 μL, 150 μL, and 200 μL of binding buffer/0.02% Tween-20. Following washing, the beads were then resuspended in 30 μL elution buffer (20 mM Tris pH 8, 100 mM NaCl, 0.02% Tween-20) and placed in a boiling water bath for 2 minutes. The beads were immediately applied to a magnetic separator and the supernatant placed in a PCR tube.

Example 7

Amplification of Selected Mannose-DNA

Thermopol buffer (1× final conc.), 60 pmol aptamerfor-biotin and 60 pmol aptamerrev, dNTPs (200 μM final conc.), 4 U Vent(exo) polymerase and $H_2O$ were added to a final volume of 200 μL. The reaction was separated into 3 tubes and cycled at:
1) 95° C. for 1.5 minutes,
2) 95° C. for 15 seconds,
3) 64° C. for 20 seconds,
4) 72° C. for 10 seconds,
5) Cycles 2 through 4 repeated for 12 cycles.

Note: Cycle number was empirically determined by removing the PCR tubes at varying cycle numbers (8-12) and running a portion (5 μL) of the reaction product on an agarose gel. Subsequently, all tubes are brought up to the optimal cycle number. It is important to avoid excessive cycling as this can lead to unwanted side reactions.

Example 8

Library Regeneration

30 U Exonuclease I was added followed by incubation at 37° C. for 30 minutes and inactivation at 80° C. for 20 minutes to remove excess primer from the previous PCR reaction. 4 M NaCl was added to a final concentration of 500 mM and EDTA was added to a final concentration of 5 mM. The PCR product was then incubated with streptavidin magnetic beads for 30 minutes with intermittent mixing. The beads were washed twice with wash buffer (20 mM Tris pH 8.0, 500 mM NaCl) followed by the addition of 40 µL 100 mM NaOH for 4 minutes to elute the unbiotinylated strand. A magnetic rack was used to pellet the beads and the supernatant was immediately mixed with 40 µL of 1 M HCl and the solution was desalted through a Centrisep column loaded with Sephadex G-50.

Thermopol buffer (1× final concentration), library regeneration primer (40 pmol), dNTPs (200 µM each final concentration), 2 U of Vent polymerase and $H_2O$ were added to a final volume of 100 µL. The reaction was heated at 64° C. for 30 seconds followed by 2 minutes at 72° C. 30 U of Exonuclease I was added and the reaction was incubated at 37° C. for 30 minutes followed by 20 minutes at 80° C. 4 M NaCl was added to a final concentration of 500 mM and EDTA was added to a final concentration of 5 mM. The product was then incubated with streptavidin magnetic beads for 30 minutes with intermittent mixing. The beads were washed twice with wash buffer (20 mM Tris pH 8.0, 500 mM NaCl) followed by the addition of 40 µL 100 mM NaOH for 4 minutes to elute the unbiotinylated strand. A magnetic rack was used to pellet the beads and the supernatant was immediately mixed with 4 µL of 1 M HCl followed by 1 µL of 1 M Tris pH 8.

Example 9

Subsequent Rounds of Library Generation/Selection

10 µL of the 45 µL recovered from the library regeneration step were used in each subsequent round of library generation/selection. 4 U of Bst polymerase was added instead of 8 U in both steps using this enzyme. 10 pmol aptamerfor was used for the strand displacement reaction. 50 nM antibody 2G12 were used in rounds 1 and 2, 10 nM antibody in rounds 3 and 4, and 5 nM antibody in rounds 5, 6, and 7. In rounds 2, 4, and 6, the library was counterselected against protein A magnetic beads by incubation with 0.75 mg beads for 30 minutes and using the supernatant to select for antibody 2G12 binding.

Example 10

Cloning of Selected Library

After 7 rounds of library generation/selection and amplification of the selected mannose-DNA from round 7, 2 µL of the amplification PCR product was used in a 100 µL amplification reaction using Vent(exo) polymerase according to the same parameters as used previously, except primer aptamerfor was used instead of primer aptamerfor-biotin. 5 U Taq polymerase was added to the PCR product and the reaction was incubated for 30 minutes at 72° C. to ensure optimal incorporation of overhanging adenosine nucleotides at the 3' ends of both strands. A TOPO TA cloning kit was then used to clone the library according to manufacturer's instructions, using blue-white colony screening to identify positive clones. 20 white colonies were picked into LB broth and the plasmid isolated and sequenced.

Example 11

Preparation of Selected Clones for Filter Binding Assay

Clones were amplified using Vent(exo) polymerase in 100 µL reactions and 20 pmol each of primers hairpinfor and aptamerrev-biotin and the conditions/thermal cycling used previously for library amplification. In these reactions, deoxythymidine triphosphate was replaced by 5' ethynyl-deoxyuridine triphosphate. The non-biotinylated strand was isolated using streptavidin magnetic beads as described, and 1 µL of 1 M Tris pH 8 was added to the isolated strand. 10 µL isolated single-stranded DNA was used in a 25 µL reaction containing 1× Thermopol buffer, 200 µM dNTPs, 15 pmol aptamerrev-biotin, and 0.5 U Vent polymerase. The reaction was incubated at 64° C. for 30 seconds followed by 72° C. for 2 minutes. Then, 10 U exonuclease I was added and the reaction was incubated at 37° C. for 30 minutes followed by inactivation at 80° C. for 20 minutes. The reaction was transferred to a cap-less 0.5 mL microcentrifuge tube. Added to the reaction was 2.5 µL 10 mM THPTA ligand, 1 µL 25 mM $CuSO_4$, 2.5 µL of 35 mM mannose sugar-azide, and the reaction was mixed by pipetting. Then, 1 µL of fresh 250 mM sodium ascorbate was added followed by immediate mixing by pipetting. The microcentrifuge tube was quickly placed in a 5 mL round bottom flask and a rubber septum used to seal the tube, and argon was flushed into the flask for 5 minutes. The reaction was allowed to proceed for 2 hours. Then, 25 µL $H_2O$ was added and the reaction was immediately desalted twice through Centrisep desalting columns containing Sephadex G-50 superfine resin. The desalted modified DNA was then radioactively phosphorylated using polynucleotide kinase and ATP ($\gamma$-$^{32}$P) according to manufacturer's instructions. The non-biotinylated, radiolabeled strand was then isolated using streptavidin magnetic beads as described, however four washes were performed to extensively remove unincorporated $^{32}$P. 1 µL of 1 M Tris pH 8 was added and the resulting modified, labeled DNA was stored on ice or at 4° C.

Example 12

Filter Binding 2.5 µL of modified, radiolabeled DNA was added to 50 µL binding buffer/0.02% Tween-20. The solution was heated to 75° C. for 3 minutes and allowed to cool to room temperature. Then, the desired amount of antibody 2G12 was added to the solution and binding allowed for 3 hours at room temperature. The solution was then filtered through a nitrocellulose/PVDF sandwich and the radioactivity in each membrane quantified by exposure to a phosphor screen followed by phosphor imaging.

Note: Nitrocellulose was exposed to 0.4 M NaOH for 10 minutes, washed extensively with $H_2O$, and then soaked in binding buffer prior to the filter binding assay. PVDF was soaked in methanol prior to extensive washing with $H_2O$ and soaking in binding buffer prior to the filter binding assay.

Example 13

Binding

Figure 6:
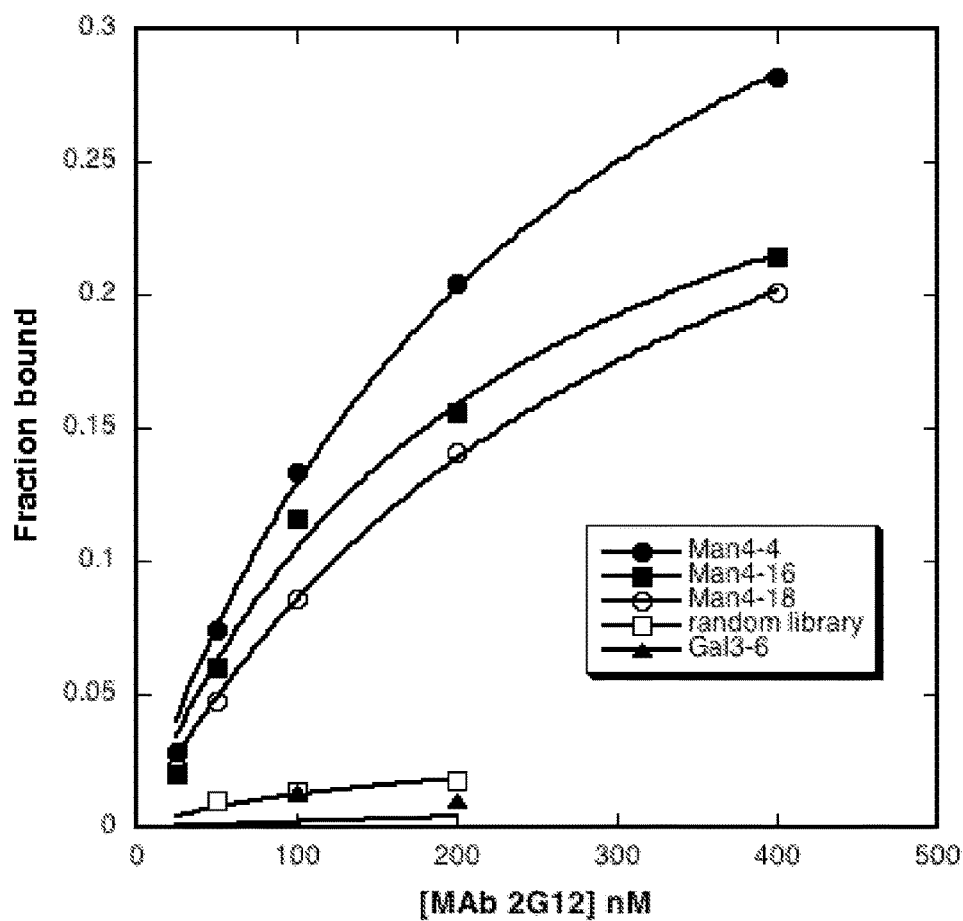
FIG. 6 depicts graphically the extent of binding to MAb 2G12 of three modified oligonucleotides. Man4-18, Man4-16 and Man4-18 bind with affinities of 270±40 nM, 220±50 nM and 330±30 nM, respectively, after 7 rounds of selection. In contrast, less than 3% of the initial random library bound to MAb2G12, and no significant binding was observed for the arbitrarily chosen sequence Gal3-6.
Figure 7:
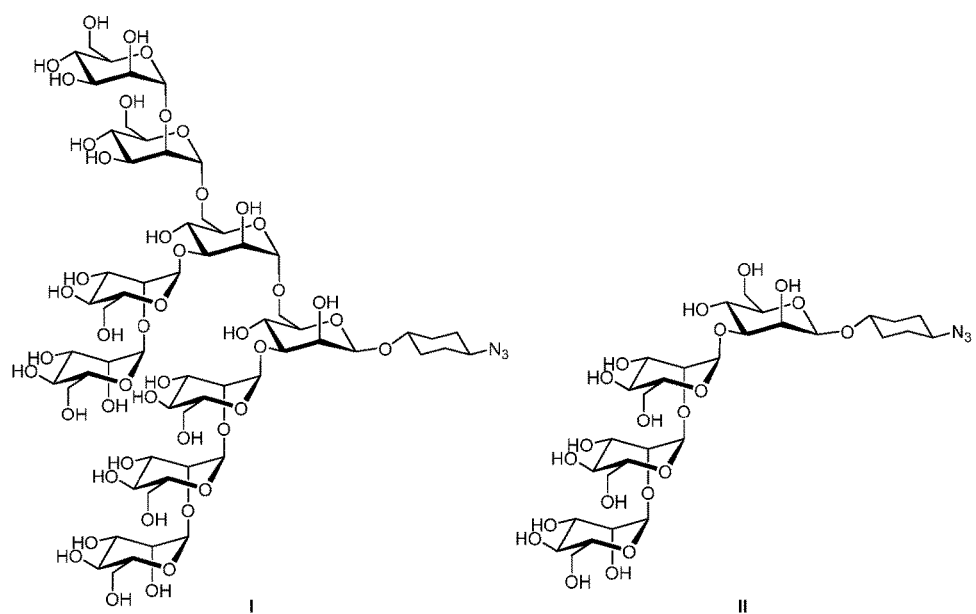
FIG. 7 depicts the structures of two oligosaccharides of the invention.
Figure 8:
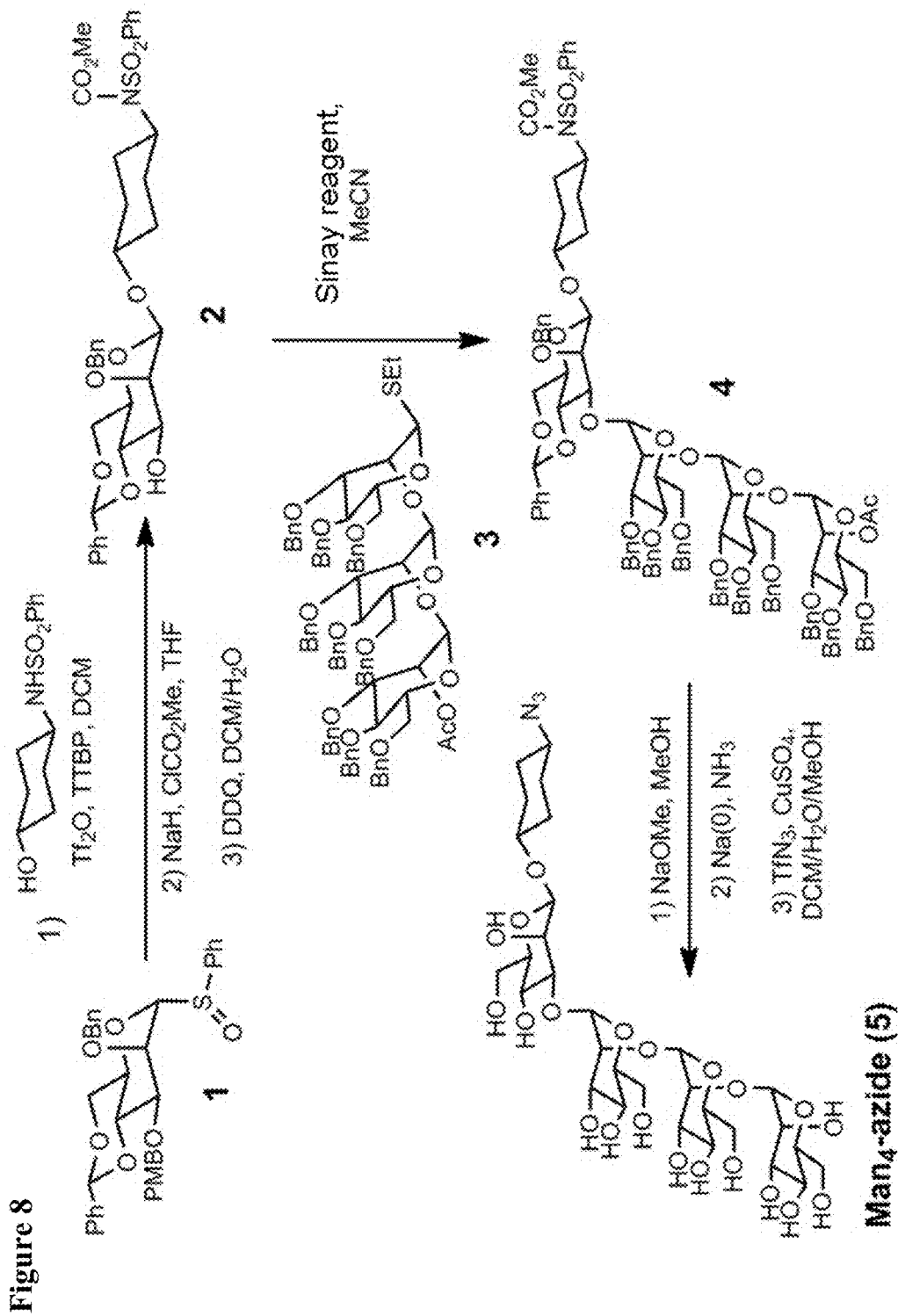
FIG. 8 depicts a route for the synthesis of oligomannan azide 5.
Figure 9:
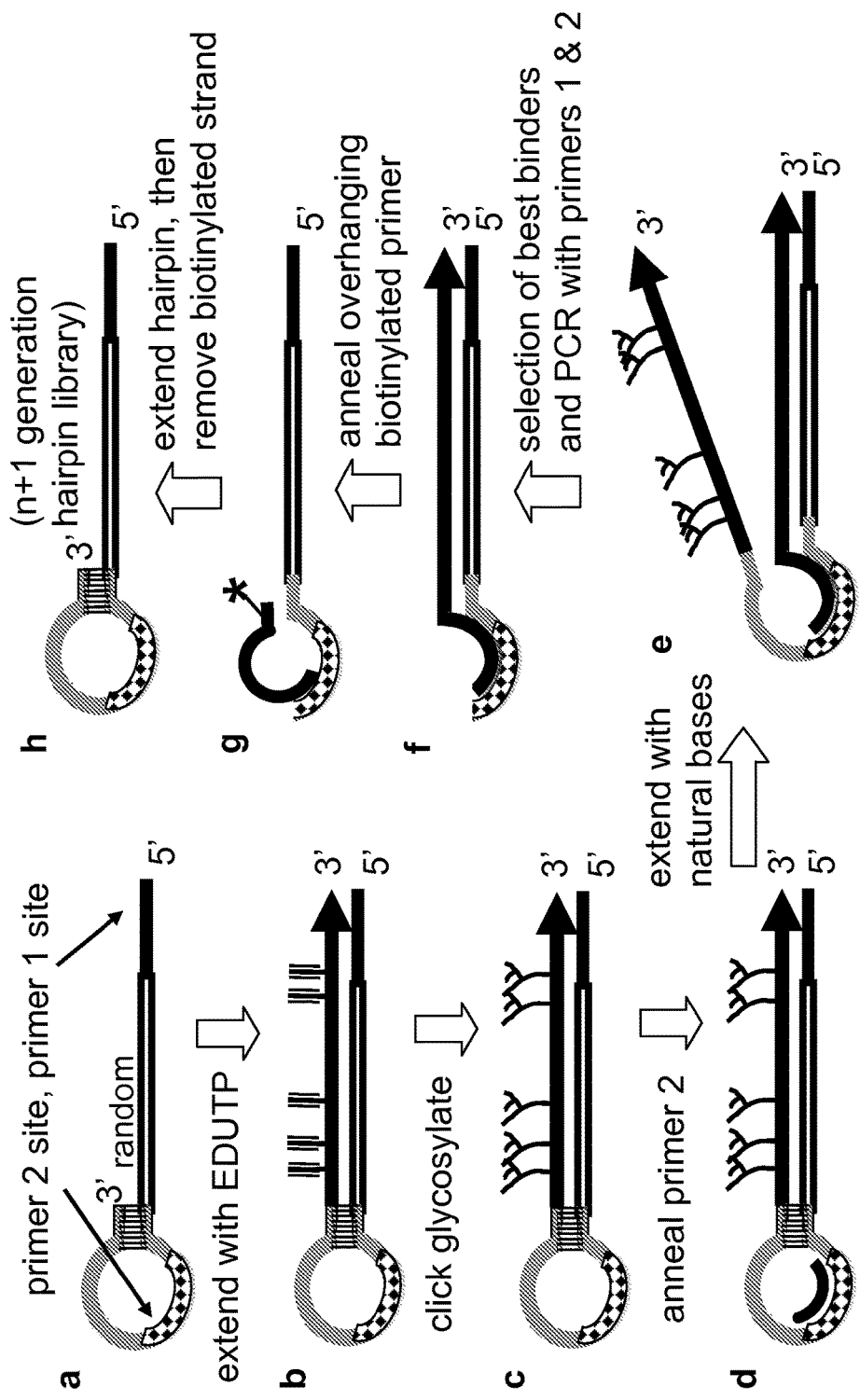
FIG. 9 is a schematic representation of a method of the invention.
Figure 10:
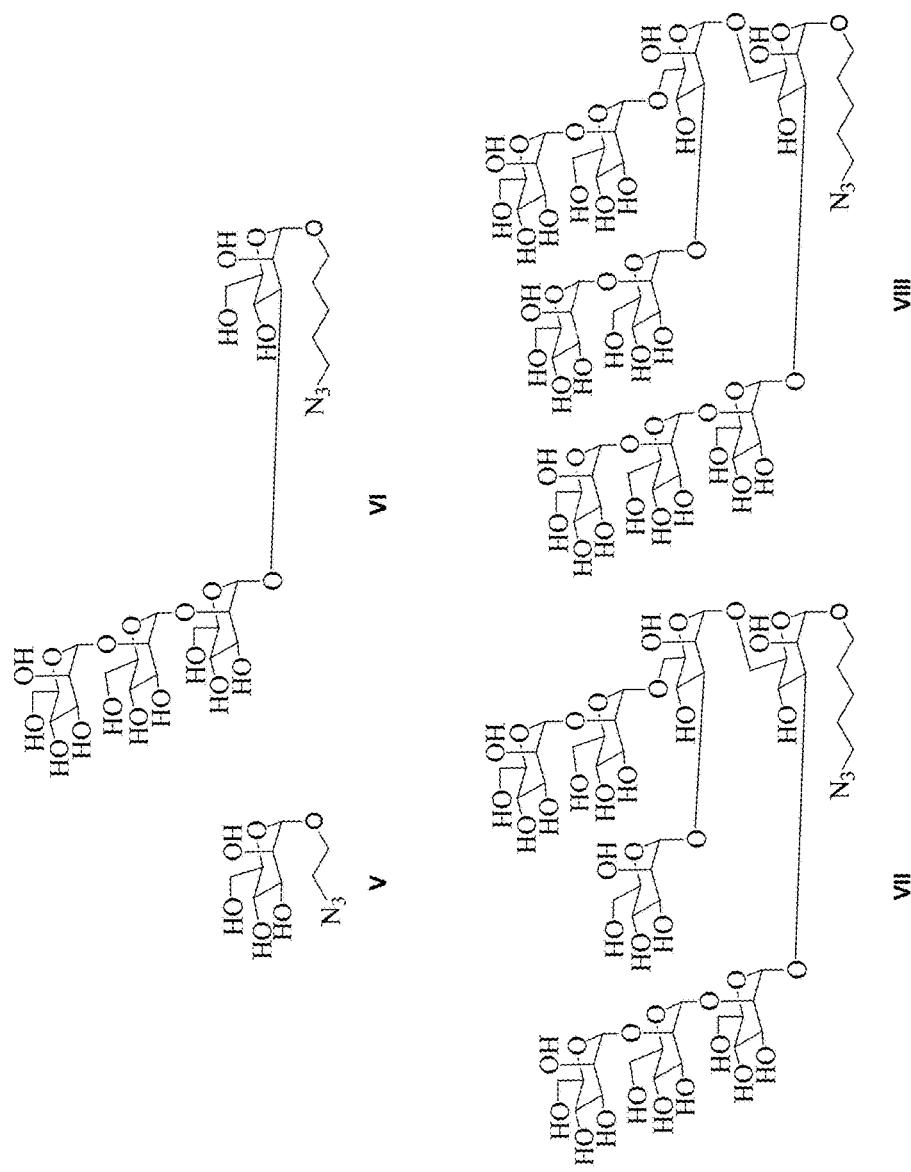
FIG. 10 depicts four additional oligosaccharide-azide compounds (V, VI, VII, and VIII) of the invention. Also contemplated are oligosaccharide-azide compounds discussed in the following: Astronomo, R. D.; et al. *Chem. Biol.* 2010, 17, 357-370; Calarese, D. A.; et al. *Proc. Natl. Acad. Sci. USA* 2005, 102, 13372-13377; Lee, H. K.; et al. *Angew. Chem. Int. Ed. Engl.* 2004, 43, 1000-1003; these articles are hereby incorporated by reference in their entireties.
Figure 11:
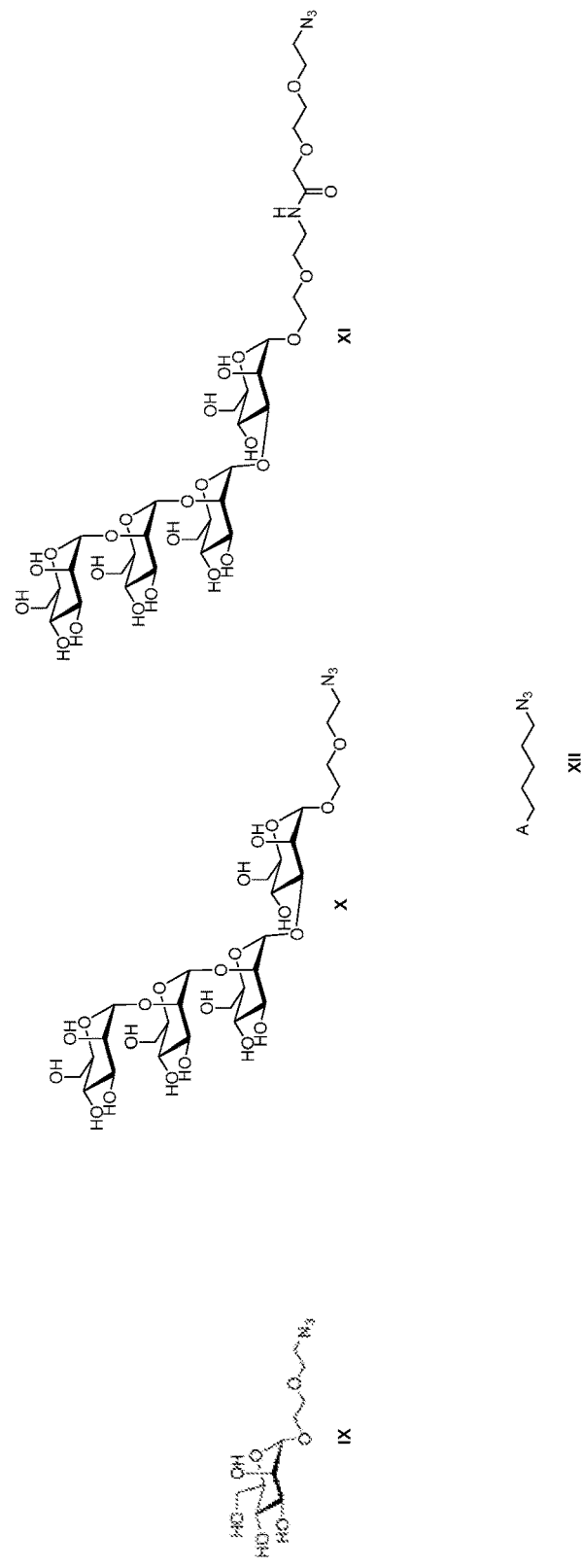
FIG. 11 depicts additional oligosaccharide-azide compounds (IX, X, XI, and XII) of the invention. In formula XII, "A" represents a branched or unbranched oligosaccharide consisting of about 3 to about 15 saccharide moieties. See Wang, J.; et al. *Org. Biomol. Chem.* 2007, 5, 1529-1540; Wang, S.-K., et al. *Proc. Natl. Acad. Sci. USA* 2008, 105(10), 3690-3695; these articles are hereby incorporated by reference in their entireties.
Figure 13:
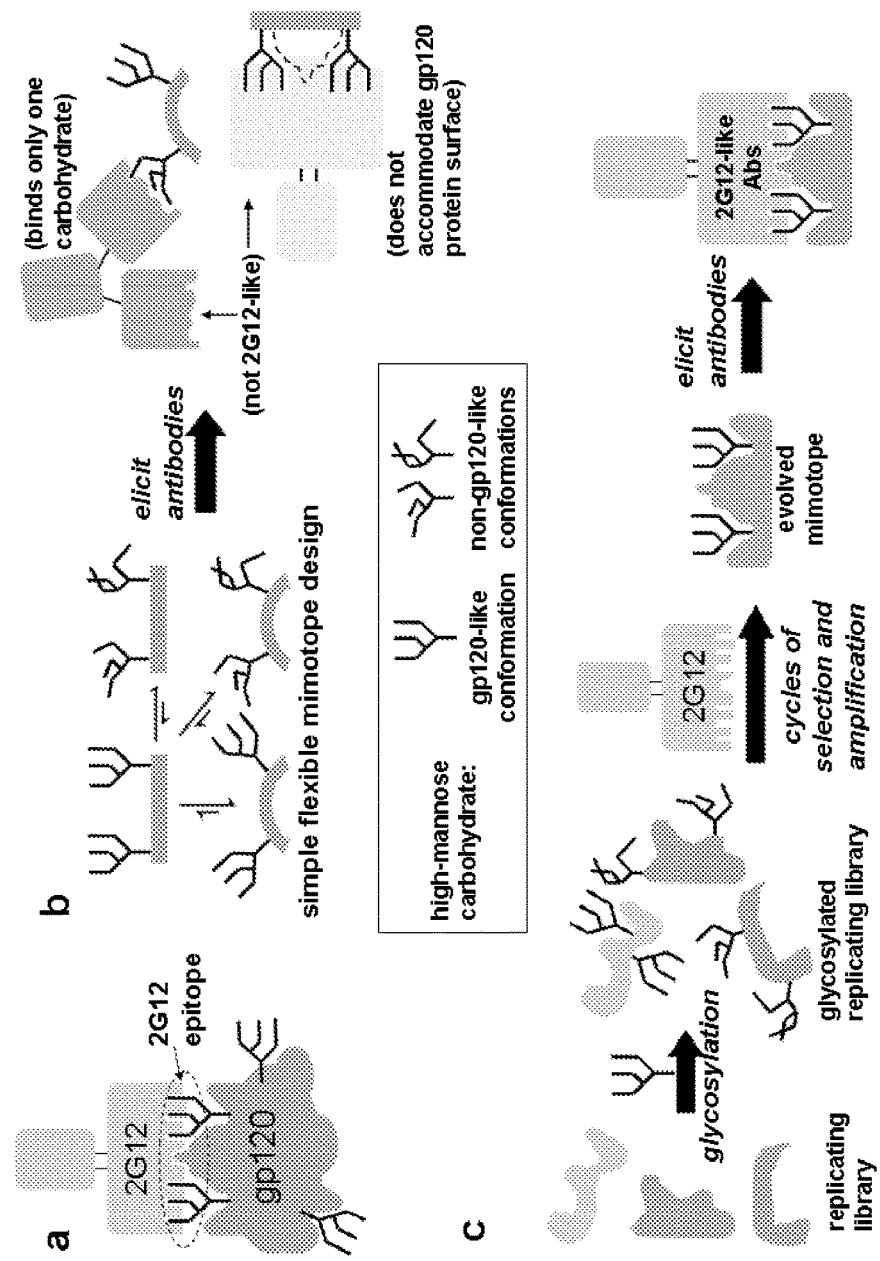
FIG. 13 depicts directed evolution approach to improved 2G12 antigen design. (a) A schematic representation of the interaction of 2G12 and gp120. Domain-exchanged antibody 2G12 binds at least two of the many high-mannose carbohydrates present on the gp120 surface, and possibly binds some of the protein surface as well. Carbohydrate conformation may be influenced by nearby peptide structure. (b) A schematic representation of carbohydrate cluster mimitopes built upon simple backbone designs. Conformations in which the carbohydrates are close enough to resemble the tightly-clustered 2G12 epitope are rare; thus, these mimitopes primarily elicit Abs recognizing single copies of glycan rather than the cluster. Even the rare cluster-specific Abs would lack pockets necessary to accommodate hypothetical gp120 protein elements (dotted surface). (c) The proposed directed-evolution-based solution to the problem of antigen design. A library of replicating glycosylated scaffolds is subjected to evolutionary pressure based on the ability to bind 2G12. The resulting evolved mimitopes contain optimal carbohydrate conformation as well as elements which mimic additional epitope components.

The results after 7 iterative rounds of selection/amplification are shown in FIG. 6. The data show that the process enriched the pool of glyco-DNAs in the library that bound to 2G12. The best binders in the library were then cloned and sequenced, and were found to show binding at the ~200-300 nM level.

Prophetic Example 14

Partial-Sequence Investigations

The minimal portion of the glyco-DNA clones' sequences necessary for binding to 2G12 will be determined. This will be accomplished through synthesis and binding evaluation of partial-sequence fragments.

Prophetic Example 15

Scale-Up

Several milligrams of glyco-DNA will be synthesized. This amount should be sufficient for immunogenicity studies as both unmodified glyco-DNA and phosphorothio-glyco-DNA.

Prophetic Example 16

Immunogenicity Studies

A small rabbit immunogenicity study will be conducted. Rabbit sera will be monitored for binding to 1) individual Man$_4$ carbohydrates, 2) the glyco-DNA immunogens, and 3) HIV gp120, as well as HIV neutralization activity.

If antibodies that bind the carbohydrates or gp120 are elicited, characterization of the antibody response and/or further immunogenicity studies of the antigens in non-human primates will follow.

Example 17

Preparation of Mutant Clones from (−)-Strand Synthetic Oligos

All synthetic mutant clones were truncated to remove the loop portion of the sequence (24 italicized residues in clone sequences in FIG. 12).

In a PCR tube, 40 pmol of (−)-strand synthetic oligo complementary to a sequence in FIG. 17, 2.5 µL 10× Thermopol buffer (New England Biolabs), 15 µL autoclaved H$_2$O, and 2 µL 25 µM primer were combined. To this was added 0.5 µL of a solution containing 10 mM deoxyadenosine triphosphate, 10 mM deoxycytosine triphosphate, 10 mM deoxyguanosine triphosphate, and 10 mM alkyne-containing thymidine triphosphate analogue 5-ethynyl-deoxyuridine (EdU) triphosphate to afford a final concentration of 200 µM each. 8 U of Bst polymerase (large fragment) was added and the mixture was incubated at 60° C. for 2 minutes to complete synthesis of the duplex. The reaction was diluted with 25 µL of autoclaved H$_2$O to a final volume of 50 µL.

For entry 21 of FIG. 17, a synthetic (+)-sense strand containing the desired sequence was simply annealed to the (−)-sense strand to produce a similar duplex structure.

The reaction was transferred into a 0.5 mL microcentrifuge tube containing 5.0 µL 10 mM THPTA ligand and 2.0 µL 25 mM CuSO$_4$. 5.0 µL of 35 mM mannose sugar-azide was added and the reaction was mixed by pipetting. Then, 2 µL of fresh 250 mM sodium ascorbate was added followed by immediate mixing by pipetting. The microcentrifuge tube was quickly placed in a 5 ml round bottom flask and a rubber septum used to seal the tube, and argon was flushed into the flask for 5 minutes. The reaction was allowed to proceed for 2 hours under argon. The modified DNA was then desalted twice through Centrisep desalting columns containing Sephadex G-50 superfine resin.

24.5 µl of the desalted modified DNA was added to a PCR tube containing 1 uL 100 mM freshly prepared dithiothreitol (DTT) and 3.0 µL T4 Polynucleotide Kinase Reaction Buffer (10×). To the reaction was added 0.5-1.0 µL ATP ($\gamma$-$^{32}$P-Perkin Elmer), followed by 10 U T4 Polynucleotide Kinase (New England Biolabs). The reaction was incubated at 37° C. for 2 hours and then the labeled product was incubated with streptavidin magnetic beads for 30 minutes at RT with rotation. The beads were washed four times with 150 µl wash buffer (20 mM Tris pH 8.0, 500 mM NaCl) followed by the addition of 40 µL 100 mM NaOH for 4 minutes to elute the unbiotinylated strand. The supernatant was immediately mixed with 4 µL of 1 M HCl followed by 1 µL of 1 M Tris pH 8.

These labeled ssDNA were then directly used in the labeling procedures as described in the filter binding section (Example 12).

Example 18

Measurement of Click Glycosylation Efficiency

The PAGE (FIG. 21a) (20% acrylamide, 29:1 acrylamide: bis-acrylamide, EtBr staining) shows the progress of the click glycosylation of clone 6 at several timepoints over two hours. Roughly 10-11 bands can be seen in the gel (corresponding to starting oligo and one-through ten-fold-glycosylated species). The identity of the 3 major bands after 2 hrs was confirmed to be the 8, 9, and 10-clicked species by RP-HPLC/ESI-MS analysis (FIG. 21b) (analysis by Novatia, Inc., 2×50 mm ACE C18 300 column, 60° C., 0.4 mL/min, 5-20% B over 19 min). See also FIG. 22.

Example 19

Synthesis of 5-ethynyl-2'-deoxyuridine-5'-triphosphate (EdUTP)

General Methods. All commercial reagents (Sigma-Aldrich, Alfa Aesar) were used as provided unless otherwise indicated. An anhydrous solvent dispensing system (J. C. Meyer) using 2 packed columns of neutral alumina was used for drying THF, Et$_2$O, and CH$_2$Cl$_2$, while 2 packed columns of molecular sieves were used to dry DMF. Solvents were dispensed under argon. Analytical HPLC was performed on a Varian Microsorb column (C18, 5µ, 4.6×250 mm) with a flow rate of 0.5 mL/min while a Varian Dynamax column (C18, 8µ, 41.4×250 mm) with a flow rate of 40 mL/min was used for preparative HPLC. An isocratic or linear gradient of 0.1 M triethylammonium bicarbonate (TEAB) and aqueous MeCN (70%) were used. Teledyne ISCO CombiFlash Rf equipped with Teledyne ISCO RediSep Rf flash column silica cartridges (www.isco.com/combiflash) were used for flash chromatography with the indicated solvent system. Nuclear magnetic resonance spectra were recorded on a Varian 600 MHz with Me₄Si, DDS or signals from residual solvent as the internal standard for $^1$H and external H$_3$PO$_4$ for $^{31}$P. Chemical shifts are reported in ppm, and signals are described as s (singlet), d (doublet), t (triplet), q (quartet), m (multiplet), brs (broad singlet), and dd (double doublet). Values given for coupling constants are first order. High resolution mass spectra were recorded on an Agilent TOF II TOF/MS instrument equipped with either an ESI or APCI interface. All reactions were performed under an inert atmosphere of dry Ar in oven dried (150° C.) glassware.

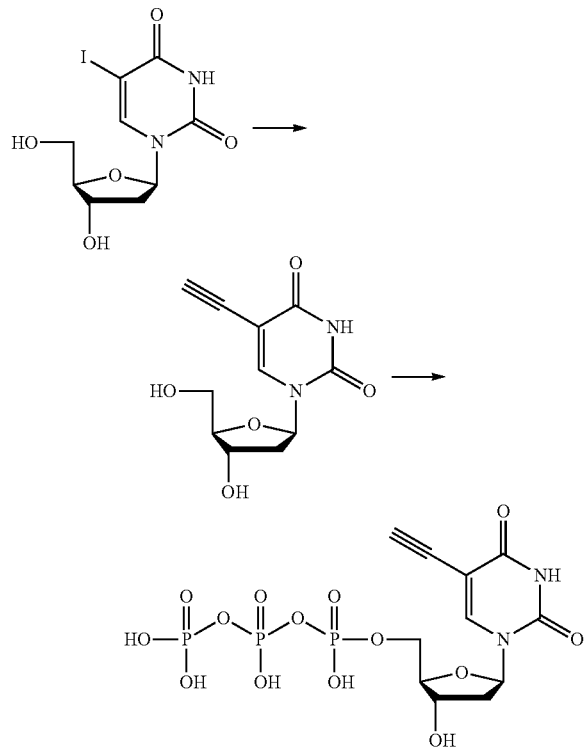

5-Ethynyl-2'-deoxyuridine. 5-Iodo-2'-deoxyuridine. (5, 1.0 g, 2.82 mmol) was dissolved in MeCN/Et₃N (66 mL of 1:1, v/v) under argon atmosphere. Trimethylsilylacetylene (1.6 mL, 11.3 mmol), bis-(triphenylphosphine)-palladium (II) chloride (42.2 mg, 0.60 mmol), and CuI (28 mg, 0.15 mmol) were added, and the mixture was heated for 3.5 h in the flask immersed into a preheated oil bath (50° C.). The solvents were removed in vacuo to give a residue that was purified by silica gel flash column chromatography. Elution with CHCl₃/MeOH (9:1, v/v) afforded trimethylsilyl intermediate as a solid (0.75 g, 82%). To the solution of this intermediate (0.7 g, 2.16 mmol) in anhydrous MeOH (16 mL) under argon atmosphere, a solution of NaOMe in MeOH (145 mL of 0.05 N) was added, and the reaction was stirred at 25° C. for 2 h. The pH of the solution was adjusted to 5-6 using Dowex 50 WX8-200 (H⁺), the mixture was filtered, and concentrated in vacuo to give a residue that was purified by silica gel column flash chromatography using CHCl₃/MeOH (8:2, v/v) as eluent to yield 5-ethynyl-2'-deoxyuridine (EdU) as a white solid (395 mg, 73%); $^1$H NMR (DMSO-d₆) δ 11.62 (s, 1H, NH), 8.29 (s, 1H, H-6), 6.10 (dd, J=6.56, 6.56 Hz, 1H, H-1'), 5.24 (d, J=4.31 Hz, 1H, C-3' OH), 5.12 (t, J=4.91 Hz, 1H, C-5' OH), 4.23 (m, 1H, H-3'), 4.10 (s, 1H, C≡CH), 3.79 (q, J=3.25, 3.25, 3.26 Hz, 1H, H-4'), 3.59 (m, 2H, H-5', H-5"), 2.16 (m, 2H, H-2', H-2"). HRMS calcd for C₁₁H₁₁N₂O₁₄ 251.0673 (M-H)⁻, found 251.0683.

5-Ethynyl-2'-deoxyuridine-5'-triphosphate. EdU was dried by coevaporation with dry pyridine, and left over P₂O₅ under vacuo overnight. The compound (75 mg, 0.3 mmol) was dissolved in solution of trimethylphosphate (2 mL), cooled in ice-bath, and a powdered Proton Sponge (96.4 mg, 0.45 mmol) was added followed by POCl₃ (30 μL, 0.33 mmol). After 2 h of stirring, a solution of tributylammonium pyrophosphate in DMF (3 mL, 1.5 mmol) containing tributylamine (300 μL, 1.26 mmol) was quickly added to the reaction mixture. After 2 min of stirring mixture was poured into 30 mL of 0.2 M TEAB, stirred and evaporated to dryness. Proton-Sponge was removed on small column with Dowex 50 WX8-200 (Na⁺). The crude product was then purified by preparative HPLC with 70% MeCN/0.1M TEAB (2-10 linear gradient) to give a residue which was dissolved in water, and passed through a small column of Dowex 50 WX8-200 (Na⁺). Fractions containing product were combined and lyophilized to give the product as a white powder (46.5 mg, 28%). $^1$H NMR (D₂O) δ 8.02 (s, 1H, H-6), 6.76 (t, J=6.59 Hz, 1H, H-1'), 4.44 (m, 1H, H-3'), 4.00 (m, 3H, H-4', H-5', H-5'), 3.39 (s, 1H, C≡CH), 2.12 (m, 2H, H-2', H-2"). $^{31}$P NMR (243 MHz, D₂O) δ ppm −8.94 (d, J=20.38 Hz), −10.49 (d, J=20.19 Hz), −22.16 (t, J=20.17 Hz). HRMS calcd for C₁₁H₁₄N₂O₁₄P₃ 490.9663 (M-H)⁻, found 490.9673.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An oligonucleotide comprising at least one non-natural deoxynucleoside to which is covalently linked a branched or unbranched oligosaccharide, wherein the oligonucleotide adopts a conformation whereby the oligonucleotide binds specifically to a monoclonal antibody having affinity for a carbohydrate epitope.

2. The oligonucleotide according to claim 1, wherein the non-natural deoxynucleoside is a substituted deoxyuridine.

3. The oligonucleotide according to claim 1, wherein the branched or unbranched oligosaccharide contains from 3 to 15 saccharide moieties.

4. The oligonucleotide according to claim 1, wherein the branched or unbranched oligosaccharide contains a plurality of mannose moieties.

5. The oligonucleotide according to claim 1, wherein the oligonucleotide comprises from about 15 to about 56 nucleosides.

6. The oligonucleotide according to claim 1, wherein the oligonucleotide comprises more than one non-natural deoxynucleoside.

7. The oligonucleotide according to claim 6, wherein the oligonucleotide comprises from 7 to 14 non-natural deoxynucleosides.

8. The oligonucleotide according to claim 1, wherein the branched or unbranched oligosaccharide is covalently linked to the non-natural deoxynucleoside by a triazole ring and a linker between the triazole ring and the oligosaccharide.

9. The oligonucleotide according to claim 8, wherein the linker comprises a linear or branched $C_2$ to $C_{18}$ alkandiyl; a linear or branched $C_2$ to $C_{30}$ alkandiyl optionally interrupted by one or more non-adjacent —O—, one or more —NR— where R is H or alkyl, or one or more —C(=O)—; a 1,3-cyclohexanediyl; a 1,4-cyclohexanediyl; 4-methyl -1,3-cyclohexanediyl; an aryl diradical; a heteroaryl diradical; a monosaccharide diradical; or a disaccharide diradical.

10. The oligonucleotide according to claim 1, wherein the monoclonal antibody is an HIV-1 neutralizing antibody.

11. The oligonucleotide according to claim 10, wherein the HIV-1 neutralizing antibody is 2G12.

12. The oligonucleotide according to claim 11, wherein the oligonucleotide comprises the sequence CCCGGC-dUGdUdUdUCAGAdUGCdUGdUAAGdU (nt 11-35 of SEQ ID NO: 26) where dU is $Man_4$-glycosylated 5-ethynyl deoxyuridine.

13. An immunogenic conjugate comprising an oligonucleotide bound to an immunogenic carrier molecule, wherein the oligonucleotide comprises at least one non-natural deoxynucleoside to which is covalently linked a branched or unbranched oligosaccharide, wherein the oligonucleotide binds specifically to an antibody.

14. The immunogenic conjugate according to claim 13, wherein the immunogenic carrier molecule is keyhole limpet hemocyanin or an outer membrane protein complex of *Neisseria meningitidis*.

15. A pharmaceutical composition comprising an oligonucleotide according to claim 1.

16. The pharmaceutical composition according to claim 15 further comprising an adjuvant.

17. The pharmaceutical composition according to claim 16, wherein the adjuvant comprises aluminum hydroxide, aluminum phosphate, or squalene.

18. A pharmaceutical composition comprising an immunogenic conjugate according to claim 13.

19. The pharmaceutical composition according to claim 18, wherein the immunogenic carrier molecule is keyhole limpet hemocyanin or an outer membrane protein complex of *Neisseria meningitidis*.

20. The pharmaceutical composition according to claim 15, wherein the oligonucleotide is present in an amount from 1µg to less than 1 mg.

21. An oligonucleotide comprising at least one non-natural deoxynucleoside and a branched or unbranched oligosaccharide covalently linked to the at least one non-natural deoxynucleoside via a linker molecule bonded to a nucleoside base of the non-natural deoxynucleoside, wherein the oligonucleotide binds specifically to a monoclonal antibody.

22. The oligonucleotide according to claim 21, wherein the non-natural deoxynucleoside is a substituted deoxyuridine.

23. The oligonucleotide according to claim 21, wherein the branched or unbranched oligosaccharide contains from 3 to 15 saccharide moieties.

24. The oligonucleotide according to claim 21, wherein the branched or unbranched oligosaccharide contains a plurality of mannose moieties.

25. The oligonucleotide according to claim 21, wherein the oligonucleotide comprises from about 15 to about 56 nucleosides.

26. The oligonucleotide according to claim 21, wherein the oligonucleotide comprises more than one non-natural deoxynucleoside.

27. The oligonucleotide according to claim 21, wherein the branched or unbranched oligosaccharide is covalently linked to the non-natural deoxynucleoside by a triazole ring and a linker between the triazole ring and the oligosaccharide.

28. The oligonucleotide according to claim 27, wherein the linker comprises a linear or branched $C_2$ to $C_{18}$ alkandiyl; a linear or branched $C_2$ to $C_{30}$ alkandiyl optionally interrupted by one or more non-adjacent —O—, one or more —NR—where R is H or alkyl, or one or more —C(=O)—; a 1,3-cyclohexanediyl; a 1,4-cyclohexanediyl; 4-methyl-1,3-cyclohexanediyl; an aryl diradical; a heteroaryl diradical; a monosaccharide diradical; or a disaccharide diradical.

* * * * *